United States Patent
Ahn et al.

(10) Patent No.: US 10,241,094 B2
(45) Date of Patent: Mar. 26, 2019

(54) MICRO HEATER, MICRO SENSOR AND MICRO SENSOR MANUFACTURING METHOD

(71) Applicant: Point Engineering Co., Ltd., Asan-si, Chungcheongnam-do (KR)

(72) Inventors: Bum Mo Ahn, Suwon-si (KR); Seung Ho Park, Hwaseong-si (KR); Sung Hyun Byun, Hwaseong-si (KR)

(73) Assignee: Point Engineering Co., Ltd., Asan-si, Chungcheongnam-do (KR)

( * ) Notice: Subject to any disclaimer, the term of this patent is extended or adjusted under 35 U.S.C. 154(b) by 100 days.

(21) Appl. No.: 15/344,672

(22) Filed: Nov. 7, 2016

(65) Prior Publication Data

US 2017/0131252 A1 May 11, 2017

(30) Foreign Application Priority Data

Nov. 11, 2015 (KR) ........................ 10-2015-0158141

(51) Int. Cl.
| | |
|---|---|
| *G01N 33/00* | (2006.01) |
| *H05B 3/06* | (2006.01) |
| *H05B 3/26* | (2006.01) |
| *H05B 3/03* | (2006.01) |
| *G01N 27/12* | (2006.01) |

(52) U.S. Cl.
CPC ....... *G01N 33/0027* (2013.01); *G01N 27/123* (2013.01); *G01N 27/128* (2013.01); *H05B 3/03* (2013.01); *H05B 3/06* (2013.01); *H05B 3/26* (2013.01)

(58) Field of Classification Search
CPC ........ G01N 33/0027; H05B 3/03; H05B 3/06; H05B 3/26
See application file for complete search history.

(56) References Cited

U.S. PATENT DOCUMENTS

| | | | |
|---|---|---|---|
| 5,464,966 A | 11/1995 | Gaitan et al. | |
| 5,756,971 A | 5/1998 | Hipp | ............................. 219/537 |
| 5,821,402 A | 10/1998 | Okajima et al. | |
| 7,861,575 B2 | 1/2011 | Jun et al. | ...................... 73/31.06 |
| 8,325,460 B2 | 12/2012 | Park et al. | .................... 361/286 |

(Continued)

FOREIGN PATENT DOCUMENTS

| | | | | |
|---|---|---|---|---|
| AT | 508 976 A1 | 5/2011 | ............. | G01N 27/12 |
| AT | 508976 A1 | 5/2011 | ............. | G01N 27/12 |

(Continued)

OTHER PUBLICATIONS

European Patent Office, Extended European Search Report—Application No. 16197289.8-1554 dated Mar. 16, 2017, 8 pages.

(Continued)

*Primary Examiner* — Krishnan S Menon
*Assistant Examiner* — Dwan A Gerido
(74) *Attorney, Agent, or Firm* — Sunstein Kann Murphy & Timbers LLP

(57) ABSTRACT

A micro heater includes a substrate formed of an anodized film and a heater electrode formed on the substrate and provided with a heat generation wiring line. The heat generation wiring line is formed in a laminated state. Also disclosed are a micro sensor and a micro sensor manufacturing method.

6 Claims, 16 Drawing Sheets

(56) References Cited

U.S. PATENT DOCUMENTS

| | | | |
|---|---|---|---|
| 8,354,729 B2 | 1/2013 | Hsieh et al. | |
| 10,015,841 B2 | 7/2018 | Ahn et al. | |
| 2002/0104758 A1* | 8/2002 | Mizutani | G01N 27/419 204/427 |
| 2002/0118027 A1 | 8/2002 | Routkevitch et al. | 324/694 |
| 2004/0056016 A1* | 3/2004 | Tian | F27B 17/0025 219/408 |
| 2004/0195096 A1 | 10/2004 | Tsamis et al. | |
| 2004/0213702 A1 | 10/2004 | Ingrisch | |
| 2005/0139993 A1 | 6/2005 | Lee et al. | |
| 2007/0056951 A1 | 3/2007 | Takigawa | |
| 2007/0062812 A1 | 3/2007 | Weber et al. | |
| 2008/0134753 A1 | 6/2008 | Jun et al. | |
| 2009/0151429 A1 | 6/2009 | Jun et al. | |
| 2010/0134948 A1* | 6/2010 | Park | G01N 27/223 361/286 |
| 2015/0021716 A1 | 1/2015 | Lee et al. | |
| 2015/0285754 A1* | 10/2015 | Park | G01N 27/12 257/414 |
| 2016/0084787 A1 | 3/2016 | Ahn et al. | |
| 2016/0370336 A1 | 12/2016 | Ahn et al. | H01N 33/0027 |

FOREIGN PATENT DOCUMENTS

| | | | | |
|---|---|---|---|---|
| EP | 2 533 037 A1 | 12/2012 | | G01N 27/12 |
| JP | 2006-153512 | 6/2006 | | G01N 27/22 |
| JP | 2011-149889 A | 8/2011 | | G01N 27/16 |
| JP | 2012-68069 A | 4/2012 | | G01N 27/409 |
| JP | 2012-98232 A | 5/2012 | | G01N 25/30 |
| JP | 2012-253082 A | 12/2012 | | |
| KR | 10-2009-0061864 | 6/2009 | | G01N 1/22 |
| KR | 10-2009-0064693 | 6/2009 | | B81C 1/00 |
| KR | 10-2010-0054526 A | 5/2010 | | G01N 27/12 |
| KR | 10-1019576 | 3/2011 | | G01N 27/12 |
| KR | 10-2014-0106082 | 9/2014 | | G01N 27/403 |
| KR | 10-2014-0118021 | 10/2014 | | G01N 27/407 |
| KR | 10-2015-0010473 A | 1/2015 | | G01N 27/12 |
| WO | WO 2009/026592 A1 | 2/2009 | | |

OTHER PUBLICATIONS

Korea Intellectual Property Office, Notice of Request for Submission of Opinions dated Feb. 15, 2017 pertaining to Application No. 10-2015-0158141, 7 pages (*In Korean*).

Korea Intellectual Property Office, Notice of Request for Submission of Opinions dated Feb. 15, 2017 pertaining to Application No. 10-2015-0158141, 8 pages (*English Translation*).

Kim et al., "Capacitive humidity sensor design based on anodic aluminum oxide", Sensors and Actuators B: Chemical: International Journal Devoted to Research and Development of Physical and Chemical Transducers, Elsevier, vol. 141, No. 2, pp. 441-446, Sep. 7, 2009.

United States Patent and Trademark Office, Non-Final Office Action—U.S. Appl. No. 14/864,184, dated Nov. 8, 2017, 51 pages.

European Patent Office, Communication pursuant to Article 94(3) EPC, Application No. 16197289.8, dated Aug. 30, 2018, 6 pages.

* cited by examiner

MICRO HEATER, MICRO SENSOR AND MICRO SENSOR MANUFACTURING METHOD

CROSS-REFERENCE TO RELATED PATENT APPLICATION

This U.S. non-provisional patent application claims priority under 35 U.S.C. § 119 of Korean Patent Application No. 10-2015-0158141 filed on Nov. 11, 2015 in the Korean Patent Office, the entire contents of which are hereby incorporated by reference.

TECHNICAL FIELD

The present invention relates to a micro heater, a micro sensor and a micro sensor manufacturing method, which make use of an anodized film.

BACKGROUND

As an interest on an environment gradually increases in recent years, a demand has existed for the development of a small-size sensor capable of accurately obtaining different kinds of information within a short period of time. Particularly, for the purpose of making a residential space pleasant, coping with a harmful industrial environment and managing a production process of beverage and foodstuff, efforts have been made to achieve the size reduction, precision enhancement and price reduction of a micro sensor such as a gas sensor for measuring a gas concentration or the like.

The currently available gas sensor gradually evolves from a ceramic-sintered gas sensor or a thick-film-type gas sensor to a micro gas sensor having the form of a micro electro mechanical system (MEMS) due to the application of a semiconductor process technique.

From the viewpoint of a measurement method, a method of measuring a change in the electric characteristics of a sensing material of a sensor when a gas is adsorbed to the sensing material is most frequently used in the currently available gas sensor. Typically, a metal oxide such as $SnO_2$ or the like is used as the sensing material to measure a change in the electrical conductivity depending on the concentration of a measurement target gas. This measurement method has an advantage in that it is relatively easy to use the method. A change in the measurement value becomes conspicuous when the metal oxide sensing material is heated to and operated at a high temperature. Accordingly, accurate temperature control is essential in order to rapidly and accurately measure a gas concentration. Furthermore, the gas concentration is measured after the sensing material is reset or restored to an initial state by forcibly removing gas species or moisture already adsorbed to the sensing material through high-temperature heating. Thus, the temperature characteristics in the gas sensor directly affect major measurement factors such as the sensor measurement sensitivity, the restoration time, the reaction time and the like.

Accordingly, a micro heater configured to locally and uniformly heat only the region of a sensing material is effective for efficient heating. However, if a large amount of electric power is consumed in controlling a temperature when measurement is performed by a micro gas sensor, it is necessary to use a large battery or a large power supply source although the volume of a sensor and a measurement circuit remains small. This may decide the overall size of a measurement system. Thus, in order to realize a micro gas sensor, a structure having small power consumption need to be preferentially taken into account.

Thus far, a silicon substrate having extremely large heat conductivity has been predominantly used in manufacturing most of micro gas sensors. Therefore, in order to reduce a heat loss, an etched pit or groove is formed in a sensor structure through a bulk macro-machining, thereby forming a suspended structure separated from a substrate. Thereafter, a micro heater, an insulation film and a sensing material are sequentially formed on the suspended structure. This makes it possible to partially reduce a heat transfer loss. However, this method is a manufacturing method primarily focused on wet etching that makes use of the crystal directivity of the substrate. Thus, this method has a limit in reducing the size of a sensor element. Furthermore, there is a problem in that the physical property of an etchant such as KOH (potassium hydroxide) or the like used in this method lacks compatibility with a standard CMOS semiconductor process.

FIG. 1 is a perspective view of a humidity sensor, one of micro sensors of the related art. The humidity sensor 10 includes a substrate 11, a porous anodic aluminum oxide (AAO) layer 13 formed on the substrate 11, and an electrode 15 formed on the porous anodic aluminum oxide layer 13.

The substrate 11 is made of aluminum and is formed in a substantially rectangular plate shape. The porous anodic aluminum oxide layer 13 is formed by oxidizing the substrate 11. If aluminum is oxidized, it is possible to form the porous anodic aluminum oxide layer 13 having a plurality of holes 13a formed on the surface thereof. A barrier layer is formed between the porous anodic aluminum oxide layer 13 and the substrate 11.

In this case, the holes 13a are formed to have a diameter of 60 nm or less. By forming the holes 13a to have a diameter of 60 nm or less, it is possible to prevent the holes 13a from being damaged by an etching solution. The electrode 15 is made of metal such as platinum, aluminum, copper or the like. The electrode 15 may be formed by different methods such as a vapor deposition method or the like.

The electrode 15 includes a first electrode 16 and a second electrode 17 disposed adjacent to the first electrode 16. The first electrode 16 has a plurality of electrode projections 16a protruding toward the second electrode 17. The second electrode 17 has a plurality of electrode projections 17a protruding toward the first electrode 16.

However, the electrode arrangement of the related art has a problem in that it is difficult to secure a heat generation quantity enough to heat a sensing material to a high temperature.

PRIOR ART DOCUMENTS

Patent Documents

Patent document 1: Korean Patent Application Publication No. 2009-0064693
Patent Document 2: Korean Patent No. 1019576

SUMMARY

In view of the problems mentioned above, it is an object of the present invention to provide a micro heater, a micro sensor and a micro sensor manufacturing method, which are capable of easily securing a heat generation amount and rapidly and accurately sensing a measurement target gas.

According to one aspect of the present invention, there is provided a micro heater, including: a substrate formed of an anodized film; and a heater electrode formed on the substrate and provided with a heat generation wiring line, wherein the heat generation wiring line is formed in a laminated state.

In the micro heater, the heat generation wiring line includes at least a first heat generation wiring line and a second heat generation wiring line laminated one above the other, and a passivation layer is formed between the first heat generation wiring line and the second heat generation wiring line.

In the micro heater, the heat generation wiring line includes a first heat generation wiring line formed on the substrate, a second heat generation wiring line laminated above the first heat generation wiring line, and a connection wiring line configured to interconnect the first heat generation wiring line and the second heat generation wiring line, and a passivation layer is formed between the first heat generation wiring line and the second heat generation wiring line.

In the micro heater, the heat generation wiring line includes a first heat generation wiring line formed on the substrate, a second heat generation wiring line at least partially formed at an upper side of a space where the first heat generation wiring line is not disposed, and a connection wiring line configured to interconnect the first heat generation wiring line and the second heat generation wiring line, and a passivation layer is formed between the first heat generation wiring line and the second heat generation wiring line.

In the micro heater, a hole is formed in the passivation layer, and the connection wiring line extends through the hole to interconnect the first heat generation wiring line and the second heat generation wiring line.

In the micro heater, the heater electrode further includes heater electrode pads respectively connected to one end of the first heat generation wiring line and one end of the second heat generation wiring line.

In the micro heater, the heater electrode is formed to continuously extend from one of the heater electrode pads to the other of the heater electrode pads.

The micro heater further includes: air gaps formed around the heat generation wiring line.

The micro heater further includes: air gaps formed around the passivation layer.

In the micro heater, the air gaps are spaces extending from an upper surface of the substrate to a lower surface of the substrate.

In the micro heater, the air gaps are discontinuously formed in a plural number.

In the micro heater, the heat generation wiring line includes a plurality of spaced-apart straight line portions formed in a straight line shape and a plurality of connection portions configured to interconnect the straight line portions.

In the micro heater, the heat generation wiring line includes a curvilinear portion formed in at least a portion thereof.

In the micro heater, each of the first heat generation wiring line and the second heat generation wiring line includes a plurality of spaced-apart straight line portions formed in a straight line shape and a plurality of connection portions configured to interconnect the straight line portions, and the straight line portions of the second heat generation wiring line are laminated above the straight line portions of the first heat generation wiring line.

According to another aspect of the present invention, there is provided a micro sensor, including: a substrate formed of an anodized film; a sensor electrode formed on the substrate; and a heater electrode formed on the substrate and provided with a heat generation wiring line, wherein the heat generation wiring line is formed in a laminated state.

In the micro sensor, the heat generation wiring line includes at least a first heat generation wiring line and a second heat generation wiring line laminated one above the other, and a passivation layer is formed between the first heat generation wiring line and the second heat generation wiring line.

In the micro sensor, the heat generation wiring line includes a first heat generation wiring line formed on the substrate, a second heat generation wiring line laminated above the first heat generation wiring line, and a connection wiring line configured to interconnect the first heat generation wiring line and the second heat generation wiring line, and a passivation layer is formed between the first heat generation wiring line and the second heat generation wiring line.

In the micro sensor, the heat generation wiring line includes a first heat generation wiring line formed on the substrate, a second heat generation wiring line at least partially formed at an upper side of a space where the first heat generation wiring line is not disposed, and a connection wiring line configured to interconnect the first heat generation wiring line and the second heat generation wiring line, and a passivation layer is formed between the first heat generation wiring line and the second heat generation wiring line.

In the micro sensor, a hole is formed in the passivation layer, and the connection wiring line extends through the hole to interconnect the first heat generation wiring line and the second heat generation wiring line.

In the micro sensor, the heater electrode further includes heater electrode pads respectively connected to one end of the first heat generation wiring line and one end of the second heat generation wiring line.

In the micro sensor, the heater electrode is formed to continuously extend from one of the heater electrode pads to the other of the heater electrode pads.

The micro sensor further includes: air gaps formed around the heat generation wiring line.

The micro sensor further includes: air gaps formed around the passivation layer.

In the micro sensor, the air gaps are spaces extending from an upper surface of the substrate to a lower surface of the substrate.

In the micro sensor, the air gaps are discontinuously formed in a plural number.

In the micro sensor, the heat generation wiring line includes a plurality of spaced-apart straight line portions formed in a straight line shape and a plurality of connection portions configured to interconnect the straight line portions.

In the micro sensor, the heat generation wiring line includes a curvilinear portion formed in at least a portion thereof.

In the micro sensor, each of the first heat generation wiring line and the second heat generation wiring line includes a plurality of spaced-apart straight line portions formed in a straight line shape and a plurality of connection portions configured to interconnect the straight line portions, and the straight line portions of the second heat generation wiring line are laminated above the straight line portions of the first heat generation wiring line.

According to a further aspect of the present invention, there is provided a micro sensor, including: a substrate formed of an anodized film; a first sensor electrode formed on the substrate, the first sensor electrode including a first sensor wiring line and a first sensor electrode pad connected to the first sensor wiring line; a second sensor electrode spaced apart from the first sensor electrode, the second sensor electrode including a second sensor wiring line formed on the substrate and a second sensor electrode pad connected to the second sensor wiring line; a heater electrode including a heat generation wiring line formed to at least partially surround the first sensor wiring line and the second sensor wiring line, and first and second heater electrode pads connected to opposite ends of the heat generation wiring line and spaced apart from each other; and a plurality of air gaps discontinuously formed around the heat generation wiring line, wherein the heat generation wiring line includes a first heat generation wiring line formed on the substrate, a second heat generation wiring line laminated above the first heat generation wiring line and configured to at least partially surround the first sensor wiring line and the second sensor wiring line, and a connection wiring line configured to interconnect the first heat generation wiring line and the second heat generation wiring line, and a passivation layer is formed between the first heat generation wiring line and the second heat generation wiring line.

According to a still further aspect of the present invention, there is provided a micro sensor, including: a substrate formed of an anodized film; a first sensor electrode formed on the substrate, the first sensor electrode including a first sensor wiring line and a first sensor electrode pad connected to the first sensor wiring line; a second sensor electrode spaced apart from the first sensor electrode, the second sensor electrode including a second sensor wiring line formed on the substrate and a second sensor electrode pad connected to the second sensor wiring line; a heater electrode including a heat generation wiring line formed to at least partially surround the first sensor wiring line and the second sensor wiring line, and first and second heater electrode pads connected to opposite ends of the heat generation wiring line and spaced apart from each other; and a plurality of air gaps discontinuously formed around the heat generation wiring line, wherein the heat generation wiring line includes a first heat generation wiring line formed on the substrate, a second heat generation wiring line at least partially formed at an upper side of a space where the first heat generation wiring line is not disposed, and configured to at least partially surround the first sensor wiring line and the second sensor wiring line, and a connection wiring line configured to interconnect the first heat generation wiring line and the second heat generation wiring line, and a passivation layer is formed between the first heat generation wiring line and the second heat generation wiring line.

According to a yet still further aspect of the present invention, there is provided a micro sensor manufacturing method, including: forming a first heat generation wiring line and a first heater electrode pad on a substrate; forming a passivation layer so as to cover the first heat generation wiring line; forming a second heat generation wiring line and a second heater electrode pad on the passivation layer so that the second heat generation wiring line is connected to the first heat generation wiring line; forming a sensor electrode on the substrate; and forming air gaps around the passivation layer.

The present invention has the following effects.

Since the length of the heat generation wiring lines becomes longer and the heat generation region increases, it is easy to secure the heat generation amount for heating the sensing material. Thus, it is possible to rapidly and accurately sense the measurement target gas.

Furthermore, since the heat generation wiring lines are stacked one above another, it is possible to increase the length of the heat generation wiring lines without increasing the area of the substrate occupied by the heat generation wiring lines.

In addition, since the substrate is formed of a porous layer, the heat capacity of the substrate is small.

DETAILED DESCRIPTION

Figure 1:
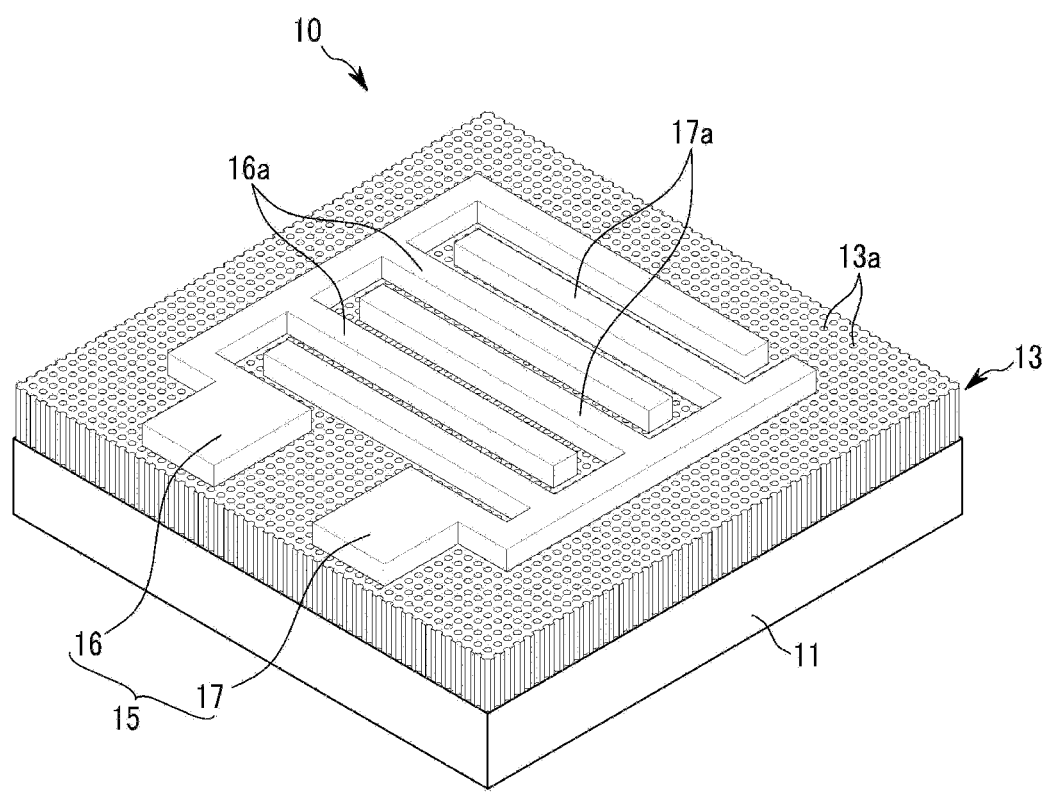
FIG. 1 is a perspective view showing a humidity sensor of the related art.

Preferred embodiments of the present invention will now be described in detail with reference to the accompanying drawings. The advantages, features and methods for achieving the same will become apparent from the following description of preferred embodiments given in conjunction with the accompanying drawings. However, the present invention is not limited to the embodiments described herein but may be embodied in many different forms. Rather, the embodiments disclosed herein are provided in order to ensure that the disclosure becomes thorough and perfect and to ensure that the concept of the present invention is sufficiently delivered to a person having an ordinary knowledge in the relevant art. The present invention is defined only by the claims. Throughout the specification, the same reference symbols designate like components.

The terms used herein are presented for the description of the embodiments but are not intended to limit the present invention. In the subject specification, a singular form includes a plural form unless specifically mentioned otherwise. By the term "comprise" or "comprising" used herein, it is meant that a component, a step, an operation or an element referred to herein does not exclude existence or addition of one or more other components, steps, operations or elements. Furthermore, the reference symbols presented in the order of descriptions is not necessarily limited to the specified order.

The embodiments disclosed herein will be described with reference to sectional views and/or plane views which are ideal exemplary views illustrating the present invention. In the drawings, the thickness of a film and a region is exaggerated to effectively describe the technical contents. Thus, the form of exemplary views may be changed depending on a manufacturing technique and/or a tolerance. For that reason, the embodiments of the present invention are not limited to specific formed illustrated in the drawings but may include changes in form generated depending on a manufacturing process. Accordingly, the regions illustrated in the drawings have general attributes. The shapes of the regions illustrated in the drawings merely illustrate specific forms of element regions and do not limit the scope of the invention.

Hereinafter, preferred embodiments of the present invention will be described in detail with reference to the accompanying drawings.

In describing different embodiments, the components for performing the same functions will be given like names and like reference numerals for the sake of convenience even in different embodiments. In addition, the configurations and operations already described in a specific embodiment will not be described in other embodiments for the sake of convenience.

For reference, the configurations identical with those of the related art among the configurations of the present invention to be described later will not be further described in detail. Reference is made to the related art described above.

As illustrated in FIGS. 2 to 5, a micro sensor provided with a micro heater according to a first preferred embodiment of the present invention includes: a substrate 100 formed of an anodized film; a sensor electrode 300 formed on the substrate 100; and a heater electrode 200 formed on the substrate 100 and provided with a heat generation wiring line 210, wherein the heat generation wiring line 210 is formed in a laminated state.

If a metallic base material is anodized, an anodized film is formed. The anodized film includes a porous layer having multiple pores formed on the surface thereof and a barrier layer existing under the porous layer. The metallic base material may be aluminum (Al), titanium (Ti), tungsten (W), zinc (Zn) or the like. It is preferred that the metallic base material is composed of aluminum or aluminum alloy which is lightweight, easy to process, superior in heat conductivity and free from contamination of heavy metal.

For example, a surface of aluminum is anodized to thereby form an aluminum oxide film which includes an aluminum oxide porous layer having multiple pores 102 formed on the surface thereof and a barrier layer existing under the aluminum oxide porous layer. The substrate 100 of the preferred embodiment of the present invention may be composed of, for example, only an aluminum oxide film from which aluminum is removed. Electrodes may be formed on the aluminum oxide porous layer of the aluminum oxide film. Alternatively, electrodes may be formed on the barrier layer. In addition, an aluminum oxide porous layer having pores 102 vertically penetrating the porous layer may be obtained by removing the barrier layer of the aluminum oxide film.

Hereinafter, descriptions will be made on the substrate 100 from which the aluminum and the barrier layer are removed.

If the aluminum and the barrier layer are removed from the anodized aluminum film, the pores 102 of the substrate 100 penetrate the substrate 100 in a vertical direction. Since the substrate 100 is formed of an aluminum oxide porous layer, the heat capacity of a micro heater decreases.

The substrate 100 includes a first support portion 110 formed at the center of the substrate 100 in a cylindrical shape, a second support portion 120 formed outside the first support portion 110 in a spaced-apart relationship with the first support portion 110, and a plurality of bridge portions 130 configured to interconnect the first support portion 110 and the second support portion 120.

The first support portion 110 is positioned in the central portion of the substrate 100. The first support portion 110 has a cylindrical shape as a whole. The bridge portions 130 are connected to the outer periphery of the first support portion 110.

Furthermore, multiple air gaps 101 are formed in the outer periphery of the first support portion 110. The air gaps 101 may be discontinuously formed. The air gaps 101 and the bridge portions 130 are alternately disposed around the first support portion 110. The bridge portions 130 are formed by discontinuously forming the air gaps 101 around the first support portion 110 through an etching process. The bridge portions 130 are connected at one end to the first support portion 110 and at the other end to the second support portion 120.

Hereinafter, descriptions will be made on the sensor electrode 300 and the heater electrode 200 formed on the upper surface of the substrate 100 according to the first embodiment.

The sensor electrode 300 is formed on the substrate 100. The sensor electrode 300 is configured to sense a change in electrical characteristic when a gas is adsorbed to a sensing material 400.

The sensor electrode 300 includes a first sensor electrode 300a and a second sensor electrode 300b disposed in a spaced-apart relationship with the first sensor electrode 300a. The first sensor electrode 300a and the second sensor electrode 300b are spaced apart in a left-right direction and are symmetrically formed with respect to a centerline vertically extending on a plane.

Each of the first sensor electrode 300a and the second sensor electrode 300b includes a sensor wiring line 310a or 310b formed on a passivation layer 150 and an upper surface of one of the bridge portions 130, and a sensor electrode pad 320 connected to the sensor wiring line 310a or 310b and formed on an upper surface of the second support portion 120.

The first sensor electrode 300a includes a first sensor wiring line 310a formed on the passivation layer 150 and one of the bridge portions 130, an a first sensor electrode pad connected to the first sensor wiring line 310a. The second sensor electrode 300b includes a second sensor wiring line 310b formed on the passivation layer 150 and one of the bridge portions 130, and a second sensor electrode pad connected to the second sensor wiring line 310b. The sensor wiring lines 310a and 310b include a first sensor wiring line 310a and a second sensor wiring line 310b. The sensor electrode pad 320 includes the first sensor electrode pad and the second sensor electrode pad. The sensor wiring lines 310a and 310b are disposed on the upper surfaces of the passivation layer 150 and one of the bridge portions 130. The sensor wiring lines 310a and 310b are formed to have a uniform width. The sensor electrode pad 320 is positioned in the second support portion 120 is formed to have a width larger than the width of the first sensor wiring line 310a and the second sensor wiring line 310b. The sensor electrode pads 320 of the first sensor electrode 300a and the second sensor electrode 300b are respectively disposed in two adjoining corners of the substrate 100 having a rectangular shape and are formed to have a width growing larger toward an outer end. In other words, the sensor electrode pads 320 are formed to have a width growing smaller toward the first sensor wiring line 310a and the second sensor wiring line 310b.

The sensor electrode 300 is made of one of Pt, W, Co, Ni, Au and Cu or a mixture containing at least one of Pt, W, Co, Ni, Au and Cu.

The heater electrode 200 is formed on the substrate 100.

In the case where the electrodes are formed on an aluminum oxide porous layer of an aluminum oxide film, the pores 102 positioned under the heater electrode 200 and the sensor electrode 300 are closed at the upper side thereof by the heater electrode 200 and the sensor electrode 300. The pores 102 are also closed at the lower side thereof. Alternatively, in the case where the electrodes are formed on a barrier layer of an aluminum oxide film, the pores 102 positioned under the heater electrode 200 and the sensor electrode 300 are closed at the upper side thereof but are opened at the lower side thereof. In the case where the barrier layer of the aluminum oxide film is removed, the pores 102 positioned under the heater electrode 200 and the sensor electrode 300 are closed at the upper side thereof by the heater electrode 200 and the sensor electrode 300. The pores 102 are opened at the lower side thereof. Since the heater electrode 200 is formed on the aluminum oxide porous layer, it is possible to provide a micro sensor having a small heat capacity.

The heater electrode 200 includes a heat generation wiring line 210 formed on the first support portion 110 and the passivation layer 150 and positioned closer to the first sensor wiring line 310a and the second sensor wiring line 310b than the sensor electrode pad 320, and heater electrode pads 290 connected to the heat generation wiring line 210 and formed on the second support portion 120 and the bridge portions 130.

As illustrated in FIGS. 2 to 5, the heat generation wiring line 210 includes a first heat generation wiring line 220 formed so as to make contact with the substrate 100, namely the upper surface of the first support portion 110, a second heat generation wiring line 240 laminated above the first heat generation wiring line 220, and a connection wiring line 255 configured to interconnect the first heat generation wiring line 220 and the second heat generation wiring line 240. When seen in a plane view, each of the first heat generation wiring line 220 and the second heat generation wiring line 240 of the heat generation wiring line 210 includes a plurality of spaced-apart straight line portions formed in a straight line shape and a plurality of connection portions configured to interconnect the straight line portions.

Figure 5:
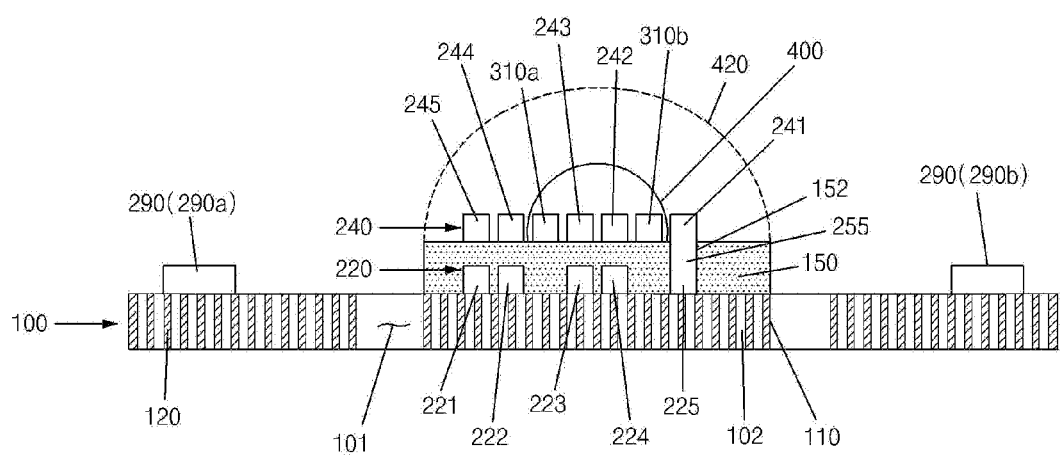
FIG. 5 is a sectional view taken along line A-A in FIG. 2.

As illustrated in FIG. 5, the passivation layer 150 as an insulation layer is formed between the first heat generation wiring line 220 and the second heat generation wiring line 240.

In the present embodiment, there is described an example in which the heat generation wiring line 210 is laminated in two layers. However, the heat generation wiring line 210 may be laminated in two or more layers.

Figure 2:
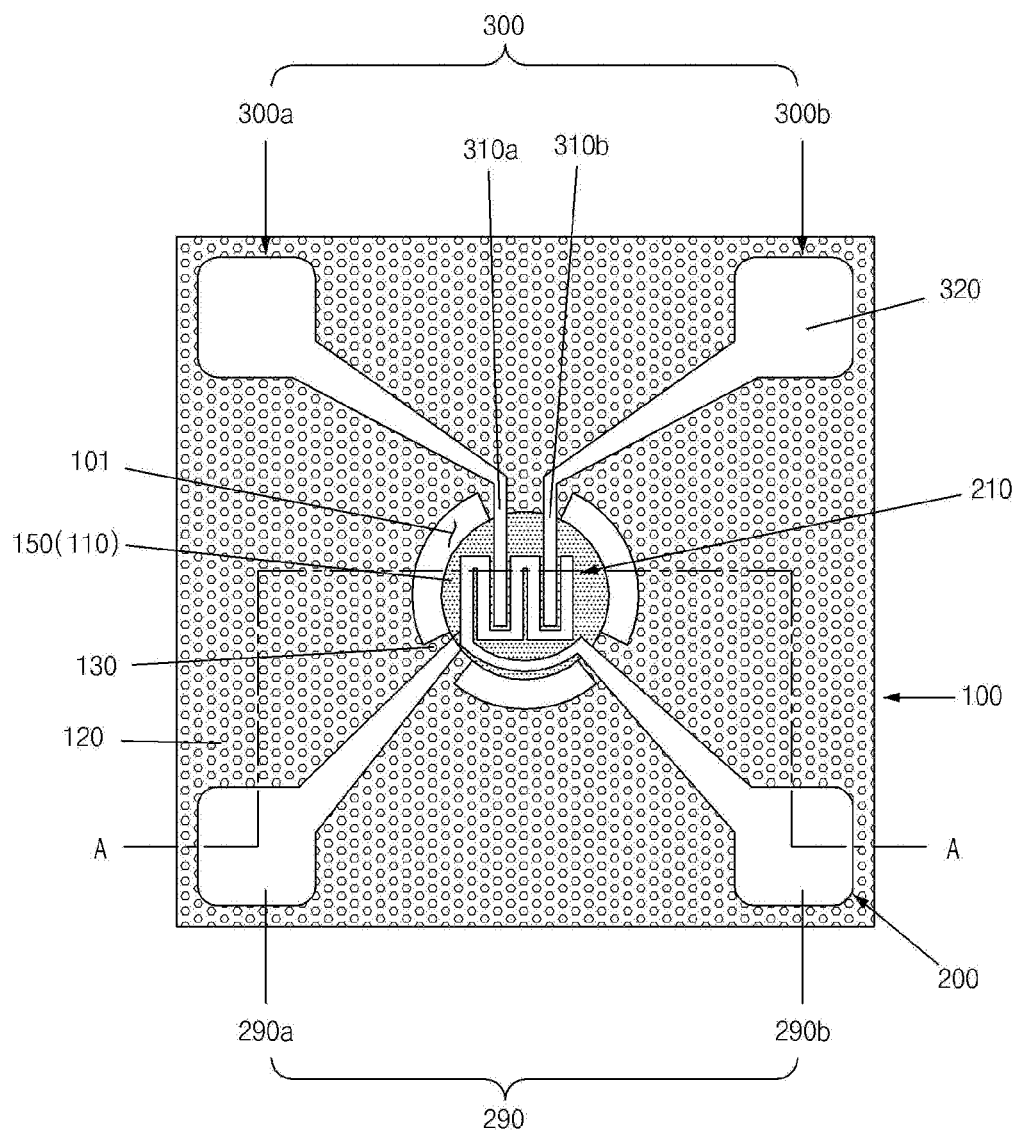
FIG. 2 is a plane view of a micro sensor provided with a micro heater according to a first preferred embodiment of the present invention (in which a sensing material and a protection layer are omitted).
Figure 3:
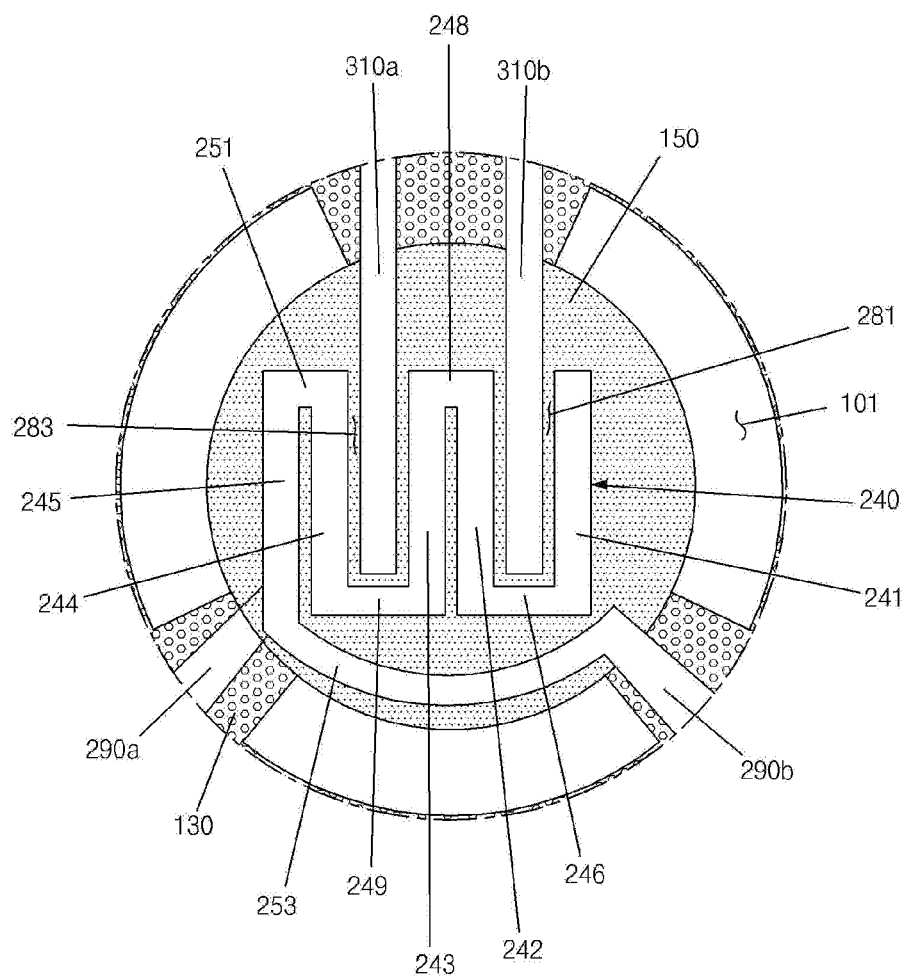
FIG. 3 is an enlarged plane view of a first support portion and an air gap portion (in which a sensing material and a protection layer are omitted).

As illustrated in FIGS. 2 and 3, the second heat generation wiring line 240 of the heat generation wiring line 210 is formed so as to at least partially surround the first sensor wiring line 310a and the second sensor wiring line 310b. The heater electrode pads 290 includes a first heater electrode pad 290a and a second heater electrode pad 290b connected to the opposite ends of the heat generation wiring line 210, namely the end portions of the first heat generation wiring line 220 and the second heat generation wiring line 240, and spaced apart from each other.

Figure 4:
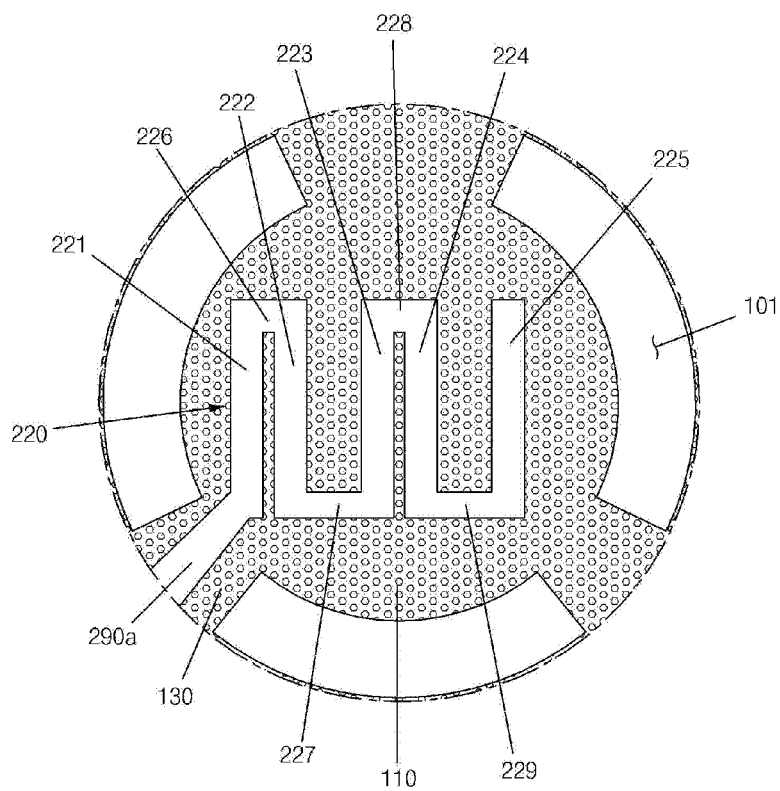
FIG. 4 is a plane view of the first support portion and the air gap portion illustrated in FIG. 3, from which a passivation layer, a second heat generation wiring line and a sensor wiring line are removed.

As illustrated in FIGS. 4 and 5, the first heat generation wiring line 220 is formed so as to make contact with the upper surface of the first support portion 110. The first heater electrode pad 290a is connected to one end portion of the first heat generation wiring line 220.

The straight line portions of the first heat generation wiring line 220 include first to fifth straight line portions 221 to 225. The connection portions of the first heat generation wiring line 220 include first to fourth connection portions 226 to 229.

As illustrated in FIG. 4, the first to fifth straight line portions 221 to 225 are formed in a straight line shape and are spaced apart from each other. One end portion of the first straight line portion 221 is connected to the first heater electrode pad 290a. Furthermore, the other end portion of the first straight line portion 221 is connected to one end portion of the second straight line portion 222 by the first connection portion 226. Thus, the first straight line portion 221, the first connection portion 226 and the second straight line portion 222 form a substantially inverted U-like shape as a whole. Furthermore, the other end portion of the second straight line portion 222 is connected to one end portion of the third straight line portion 223 by the second connection portion 227. Thus, the second straight line portion 222, the second connection portion 227 and the third straight line portion 223 form a substantially U-like shape as a whole. Furthermore, the other end portion of the third straight line portion 223 is connected to one end portion of the fourth straight line portion 224 by the third connection portion 228. Thus, the third straight line portion 223, the third connection portion 228 and the fourth straight line portion 224 form a substantially inverted U-like shape as a whole. Furthermore, the other end portion of the fourth straight line portion 224 is connected to one end portion of the fifth straight line portion 225 by the fourth connection portion 229. Thus, the fourth straight line portion 224, the fourth connection portion 229 and the fifth straight line portion 225 form a substantially inverted U-like shape as a whole.

The spaced-apart distance between the second straight line portion 222 and the third straight line portion 223 and the spaced-apart distance between heater electrode 200 fourth straight line portion 224 and the fifth straight line portion 225 are larger than the spaced-apart distance between the first straight line portion 221 and the second straight line portion 222 and the spaced-apart distance between the third straight line portion 223 and the fourth straight line portion 224.

The first heat generation wiring line 220 is formed to continuously extend from the first straight line portion 221 to the fifth straight line portion 225 via the first to fourth connection portions 226 to 229.

In the meantime, as illustrated in FIG. 5, the passivation layer 150 is formed so as to cover the upper surface of the first support portion 110 and the upper and side surfaces of the first heat generation wiring line 220. The passivation layer 150 has an electrical insulation property. The passivation layer 150 prevents the first heat generation wiring line 220 and the second heat generation wiring line 240 from making contact with each other.

The vertical height of the passivation layer 150 is larger than the vertical height of the first heat generation wiring line 220.

Figure 7:
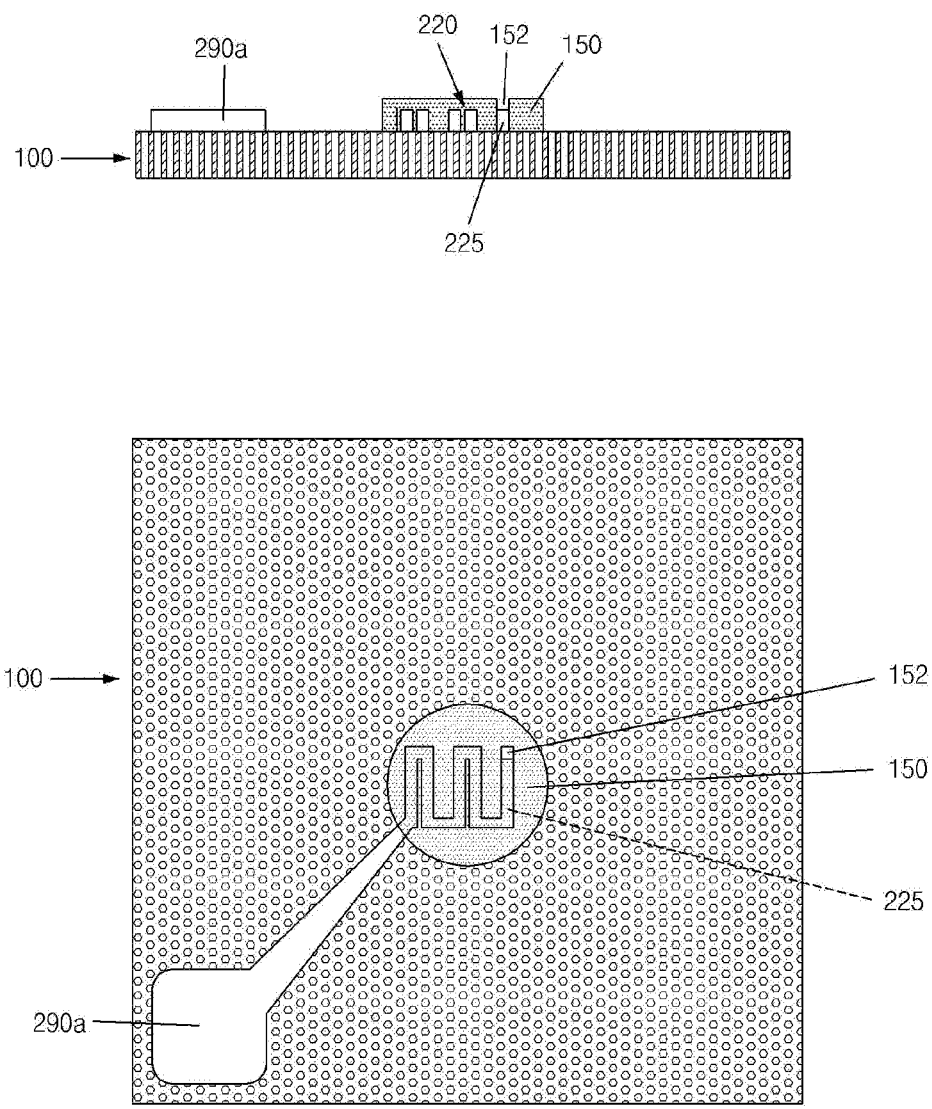

As illustrated in FIGS. 5 and 7, a hole 152 is formed in the passivation layer 150. More specifically, the hole 152 is formed above the other end portion of the fifth straight line portion 225. The other end portion of the fifth straight line portion 225 is not covered with the passivation layer 150.

One end portion of the connection wiring line 255 is connected to the other end portion of the fifth straight line portion 225. The connection wiring line 255 extends upward through the hole 152 formed in the passivation layer 150. The other end portion of the connection wiring line 255 is connected to one end portion of a sixth straight line portion 241 of the second heat generation wiring line 240. The connection wiring line 255 is formed in a perpendicular relationship with the upper surface of the first support portion 110 and is configured to interconnect the first heat generation wiring line 220 and the second heat generation wiring line 240. The connection wiring line 255 may generate heat just like the first heat generation wiring line 220 and the second heat generation wiring line 240.

As illustrated in FIGS. 3 and 5, the second heat generation wiring line 240 is formed so as to make contact with the upper surface of the passivation layer 150. The second heat generation wiring line 240 is formed above the first heat generation wiring line 220 in a spaced-apart relationship with the first heat generation wiring line 220.

The straight line portions of the second heat generation wiring line 240 include sixth to tenth straight line portions 241 to 245. The connection portions of the second heat generation wiring line 240 include a fifth connection portion 246, a seventh connection portion 248, an eighth connection portion 249 and a tenth connection portion 251. The second heat generation wiring line 240 includes a first curvilinear portion 253 configured to interconnect the tenth straight line portion 251 and the second heater electrode pad 290b.

As illustrated in FIG. 3, when seen in a plane view, the sixth to tenth straight line portions 241 to 245 are formed in a straight line shape and are spaced apart from each other. One end portion of the sixth straight line portion 241 is connected to the upper end portion of the connection wiring line 255. The other end portion of the sixth straight line portion 241 is connected to one end portion of the seventh straight line portion 242 by the fifth connection portion 246. Thus, the sixth straight line portion 241, the fifth connection portion 246 and the seventh straight line portion 242 form a substantially U-like shape as a whole.

The other end portion of the seventh straight line portion 242 is connected to one end portion of the eighth straight line portion 243 by the seventh connection portion 248. Thus, the seventh straight line portion 242, the seventh connection portion 248 and the eighth straight line portion 243 form a substantially inverted U-like shape.

Furthermore, the other end portion of the eighth straight line portion 243 is connected to one end portion of the ninth straight line portion 244 by the eighth connection portion 249. Thus, the eighth straight line portion 243, the eighth connection portion 249 and the ninth straight line portion 244 form a substantially U-like shape as a whole. Furthermore, the other end portion of the ninth straight line portion 244 is connected to one end portion of the tenth straight line portion 245 by the tenth connection portion 251. Thus, the ninth straight line portion 244, the tenth connection portion 251 and the tenth straight line portion 245 form a substantially inverted U-like shape as a whole.

The sixth to tenth straight line portions 241 to 245 are respectively disposed above the fifth straight line portion 225, the fourth straight line portion 224, the third straight line portion 223, the second straight line portion 222 and the first straight line portion 221 in a spaced-apart relationship therewith. Furthermore, the fifth connection portion 246, the seventh connection portion 248, the eighth connection portion 249 and the tenth connection portion 251 are respectively disposed above the fourth connection portion 229, the third connection portion 228, the second connection portion 227 and the first connection portion 226. Accordingly, the spaced-apart distance between the sixth straight line portion 241 and the seventh straight line portion 242 and the spaced-apart distance between the eighth straight line portion 243 and the ninth straight line portion 244 are equal to the spaced-apart distance between the fourth straight line portion 224 and the fifth straight line portion 225 and the spaced-apart distance between the second straight line portion 222 and the third straight line portion 223.

The second heat generation wiring line 240 is formed to continuously extend from the sixth straight line portion 241 to the tenth straight line portion 245 via the fifth connection portion 246, the seventh connection portion 248, the eighth connection portion 249 and the tenth connection portion 251.

As described above, the heat generation wiring line 210 is formed in a plurality of layers disposed one above another and is continuously formed in the order of the first heat generation wiring line 220, the connection wiring line 255 and the second heat generation wiring line 240.

The other end portion of the tenth straight line portion 251 is connected to the second heater electrode pad 290b by the first curvilinear portion 253. The first curvilinear portion 253 is formed to have an inflection point in the central portion thereof.

The heater electrode 200 is formed to continuously extend from the first heater electrode pad 290a, which is connected to the end portion of the first straight line portion 221, to the second heater electrode pad 290b, which is connected to the end portion of the first curvilinear portion 253.

Furthermore, the second sensor wiring line 310b and the first sensor wiring line 310a are respectively disposed in a first spaced-apart space portion 281 between the sixth straight line portion 241 and the seventh straight line portion 242 and a second spaced-apart space portion 283 between the eighth straight line portion 243 and the ninth straight line portion 244. The second heat generation wiring line 240 of the heat generation wiring line 210 is formed so as to at least partially surround the first sensor wiring line 310a and the second sensor wiring line 310b at the outer side thereof.

By laminating the heat generation wiring line 210 in an up-down direction as described above, it is possible to increase the length of the heat generation wiring line 210 without increasing the area of the substrate 100 occupied by the heat generation wiring line 210.

The heater electrode 200 is made of one of Pt, W, Co, Ni, Au and Cu or a mixture containing at least one of Pt, W, Co, Ni, Au and Cu.

The heater electrode pads 290 include a first heater electrode pad 290a and a second heater electrode pad 290b respectively connected to the opposite ends of the heat generation wiring line 210. In this way, two or more heater electrode pads 290 are formed. The heater electrode pads 290 are disposed at two adjoining corners of the substrate 100 and are formed so that the width thereof grows larger outward. In other words, the heater electrode pads 290 are formed so that the width thereof grows smaller toward the heat generation wiring line 210. The heater electrode pads 290 are formed so as to have a width larger than the width of the heat generation wiring line 210.

A discoloration-preventing protection layer (not shown) is formed on the entire upper surfaces of the heater electrode 200 and the sensor electrode 300. The discoloration-preventing protection layer may be made of an oxide-based material. Moreover, the discoloration-preventing protection layer may be made of at least one of tantalum oxide ($TaO_x$), titanium oxide ($TiO_2$), silicon oxide ($SiO_2$) and aluminum oxide ($Al_2O_3$).

Furthermore, soldering metal is formed in the end portions of the heater electrode pads 290 and the sensor electrode pads 320. The soldering metal is formed on the discoloration-preventing protection layer. The soldering metal may be at least one of gold, silver and tin.

The air gaps 101 are formed around the first support portion 110. In other words, the air gaps 101 are formed on the substrate 100 so as to surround the heat generation wiring line 210. The air gaps 101 are formed around the passivation layer 150 and the heat generation wiring line 210.

The maximum width (transverse width) of the air gaps 101 is set larger than the maximum width of the pores 102. The air gaps 101 are formed in an arc shape. The number of the air gaps 101 may be three. The air gaps 101 are spaced apart in a circumferential direction. That is to say, the air gaps 101 are discontinuously formed in a plural number.

Specifically, the air gaps 101 are disposed between the first sensor wiring line 310a and the first heater electrode pad 290a, between the first heater electrode pad 290a and the second heater electrode pad 290b and between the second heater electrode pad 290b and the second sensor wiring line 310b. The air gaps 101 are formed in a region other than the portions which support the heater electrode 200 and the sensor electrode 300.

The air gaps 101 are formed to vertically penetrate the substrate 100. That is to say, the air gaps 101 are formed to extend from the upper surface of the substrate 100 to the lower surface thereof.

Due to the existence of the air gaps 101, the first support portion 110 for supporting the heat generation wiring line 210 and the sensor wiring lines 310a and 310b, the second support portion 120 for supporting the heater electrode pads 290 and the sensor electrode pads 320, and the bridge portions 130 are formed in the substrate 100. That is to say, the air gaps 101 are formed between the first support portion 110 and the second support portion 120. Thus, the air gaps 101 and the bridge portions 130 are alternately disposed around the first support portion 110.

When seen in a plane view as in FIG. 4, the first support portion 110 is formed in a circular shape and is surrounded by the air gaps 101.

The first support portion 110 and the second support portion 120 are connected to each other by the bridge portions 130.

The first support portion 110 and the second support portion 120 are spaced apart from each other by the air gaps 101 in the regions other than the bridge portions 130. Thus, the first support portion 110 and the second support portion 120 are connected to each other by the bridge portions 130 at three points.

A sensing material 400 configured to cover the seventh straight line portion 242 and the eighth straight line portion 243 of the sensor wiring lines 310a and 310b and the second heat generation wiring line 240 is formed on the passivation layer 150. The sensing material 400 is formed by printing. If the sensing material 400 is formed by printing in this way, a mesh-like mark is left on the surface of the sensing material 400 after the sensing material 400 is formed.

By vertically laminating the heat generation wiring line 210 as described above, the length of the heat generation wiring line 210 increases and the heat generation region increases. This makes it easy to secure a heat generation amount required for heating the sensing material 400. It is therefore possible to rapidly and accurately sense a measurement target gas.

In particular, the g=heat generation wiring line 210 of the micro sensor according to the first embodiment is vertically laminated in the vicinity of the first sensor wiring line 310a and the second sensor wiring line 310b. It is therefore possible to effectively increase the temperature of the sensing material 400 positioned around the first sensor wiring line 310a and the second sensor wiring line 310b.

Furthermore, a protection layer 420 configured to cover the sensor wiring lines 310a and 310b, the second heat generation wiring line 240 and the sensing material 400 is formed on the passivation layer 150.

A micro sensor manufacturing method according to the present invention will be described with reference to FIGS. 6 to 10.

Figure 6:
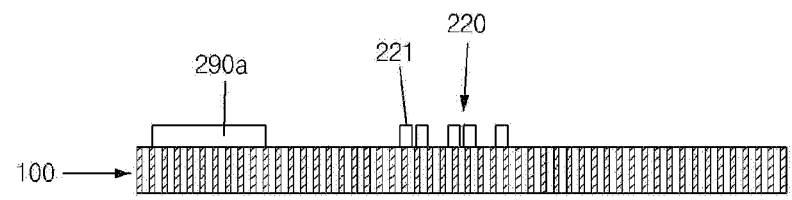
FIGS. 6 to 10 are process diagrams illustrating a micro sensor manufacturing method.
Figure 6:
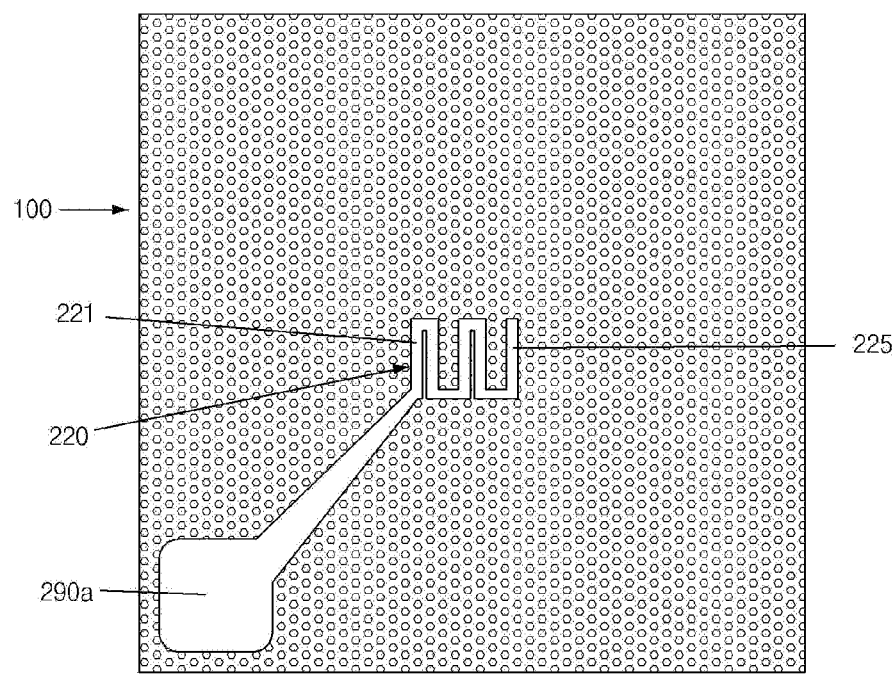

A first step is a step of forming the first heat generation wiring line 220 and the first heater electrode pad 290a on the substrate 100 as illustrated in FIG. 6.

A second step is a step of forming the passivation layer 150 so as to cover the first heat generation wiring line 220 as illustrated in FIG. 7. The other end portion of the fifth straight line portion 225 of the first heat generation wiring line 220 is not covered with the passivation layer 150 but is opened upward. In other words, the hole 152 is formed above the other end portion of the fifth straight line portion 225.

Figure 8:
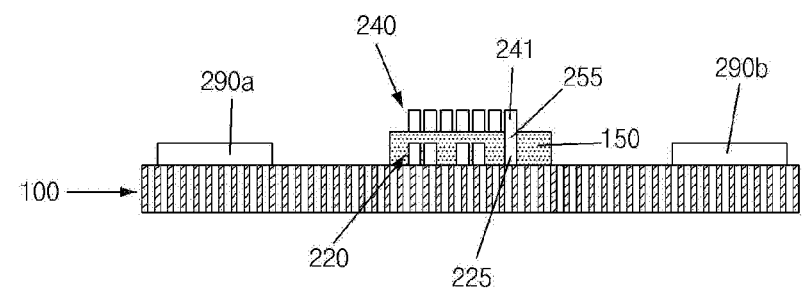
Figure 8:
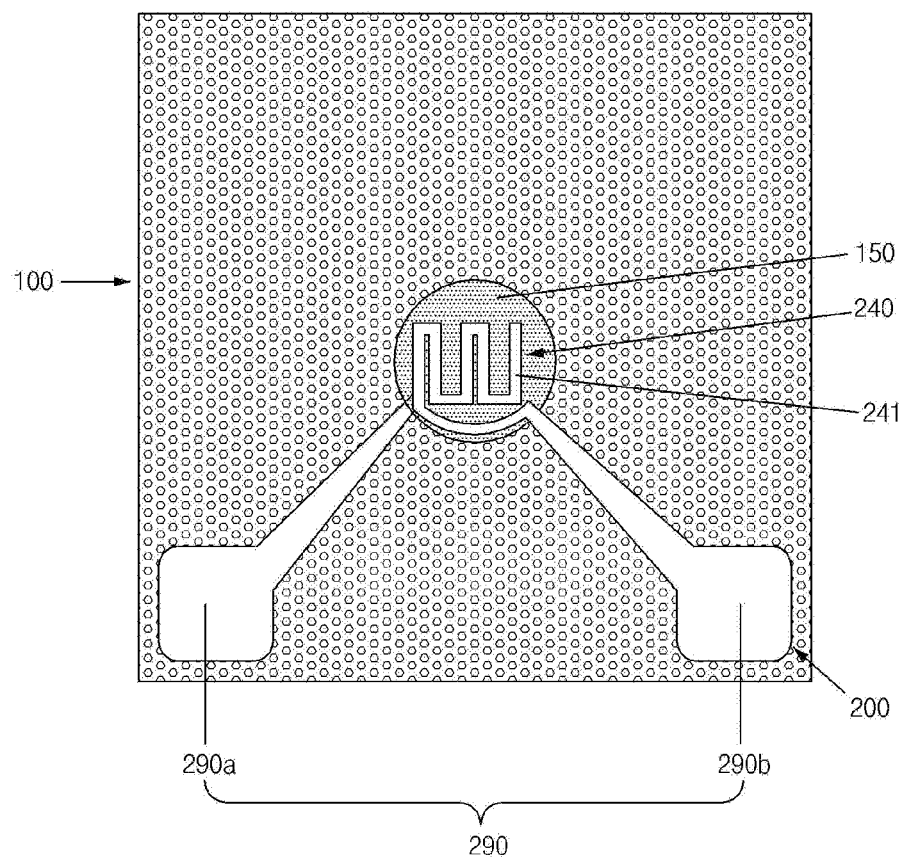

A third step is a step of forming the second heat generation wiring line 240 and the second heater electrode pad 290b on the passivation layer 150 as illustrated in FIG. 8 so that the second heat generation wiring line 240 and the second heater electrode pad 290b are connected to the first heat generation wiring line 220. The first heat generation wiring line 220 and the second heat generation wiring line 240 are connected to each other via the connection wiring line 255 inserted into the hole 152.

Figure 9:
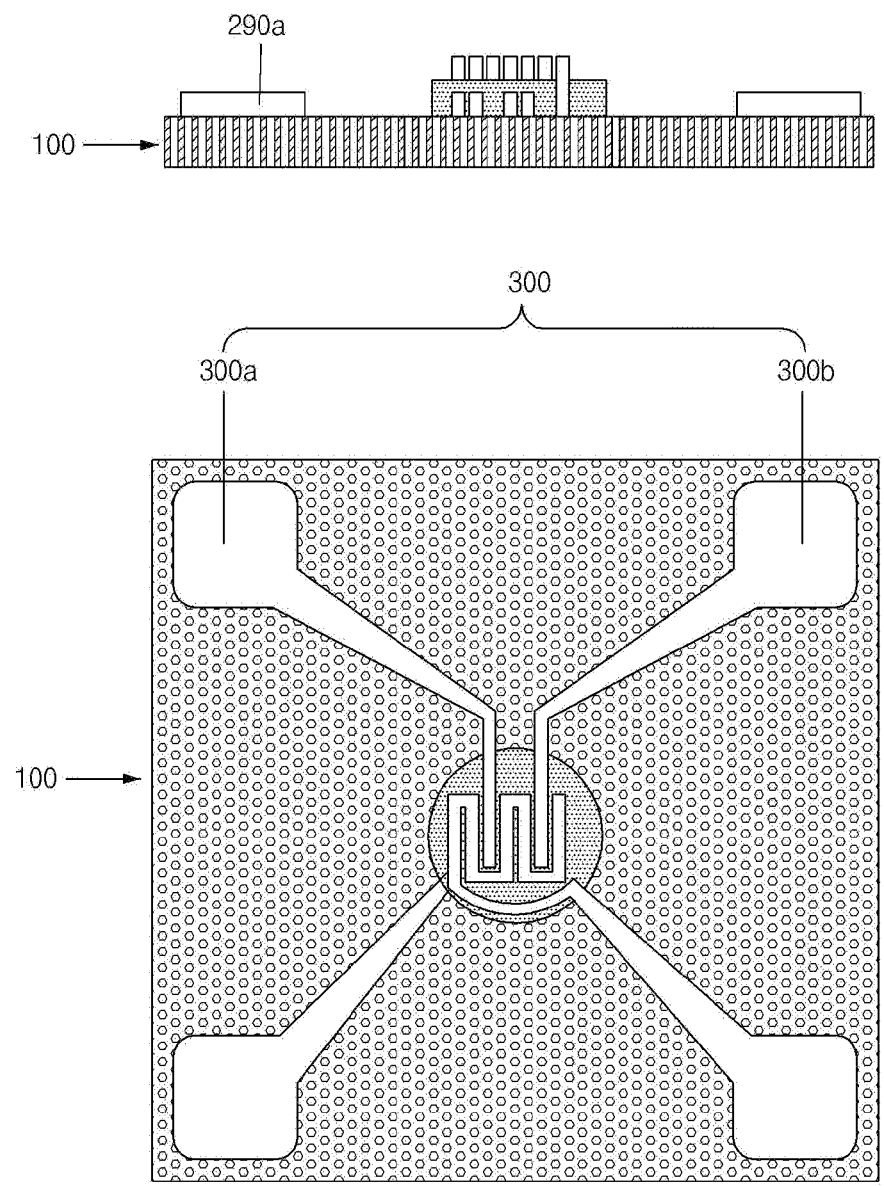

A fourth step is a step of forming the sensor electrode 300 on the substrate 100 as illustrated in FIG. 9. The first sensor wiring line 310a (see FIG. 3) and the second sensor wiring line 310b (see FIG. 3) of the sensor electrode 300 are partially formed on the passivation layer 150.

Figure 10:
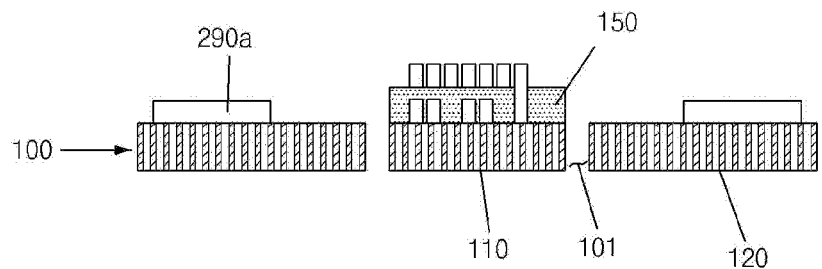
Figure 10:
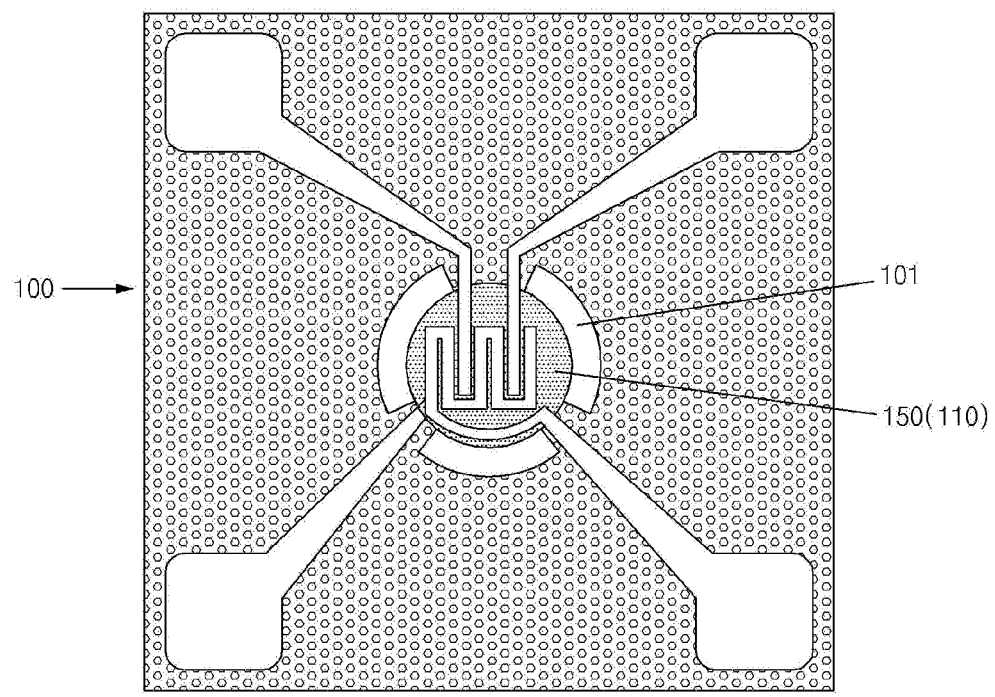
Figure 11:
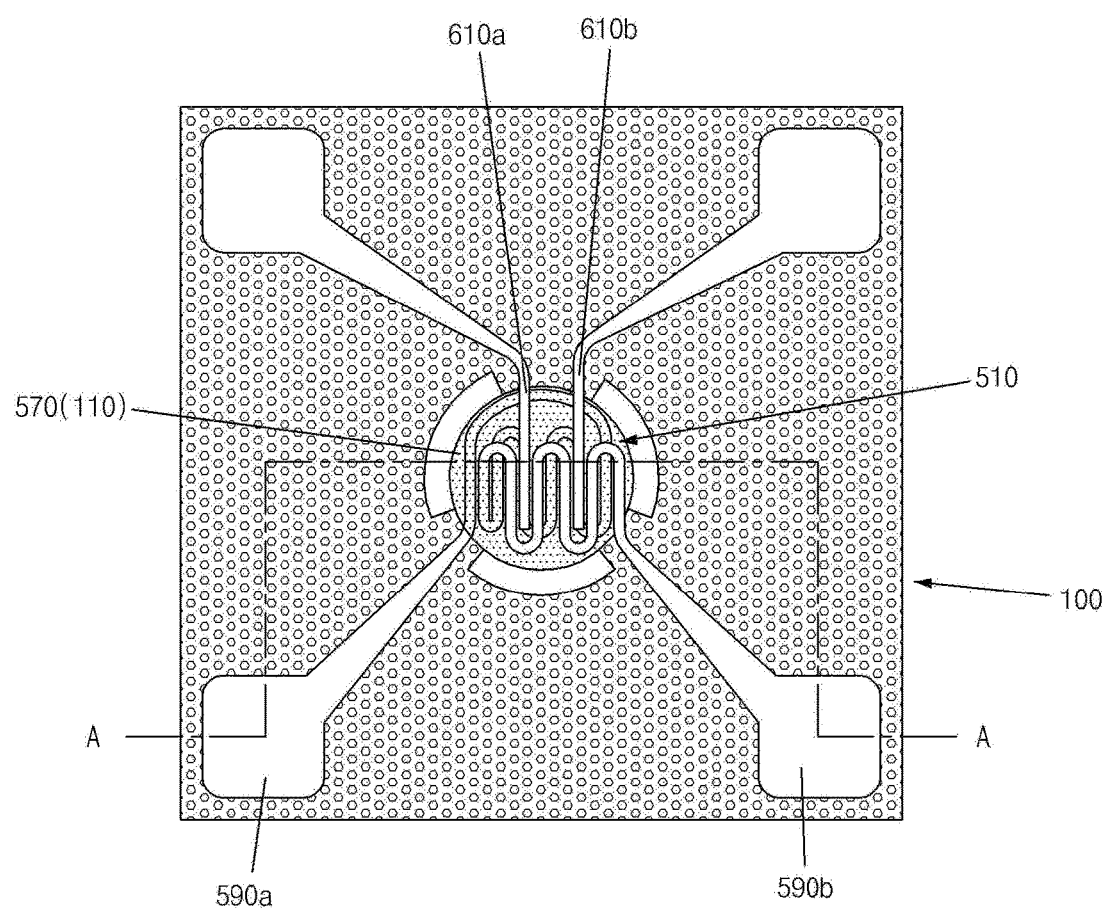
FIG. 11 is a plane view of a micro sensor provided with a micro heater according to a second preferred embodiment of the present invention (in which a sensing material and a protection layer are omitted).

A fifth step is a step of forming the air gaps 101 around the passivation layer 150 as illustrated in FIG. 10. A micro sensor can be manufactured through the steps described above.

Hereinafter, a micro sensor according to a second preferred embodiment of the present invention will be described with reference to FIGS. 11 to 14. Descriptions on the same components as those of the first embodiment will be omitted. Only a heat generation wiring line 510 differing from that of the first embodiment will be described.

The heat generation wiring line 510 according to the second embodiment includes a first heat generation wiring line 520 formed on the substrate 100, a second heat generation wiring line 540 at least partially formed at an upper side of a space 505 where the first heat generation wiring line 520 is not disposed, and a connection wiring line 560 configured to interconnect the first heat generation wiring line 520 and the second heat generation wiring line 540. A passivation layer 570 is formed between the first heat generation wiring line 520 and the second heat generation wiring line 540.

Figure 12:
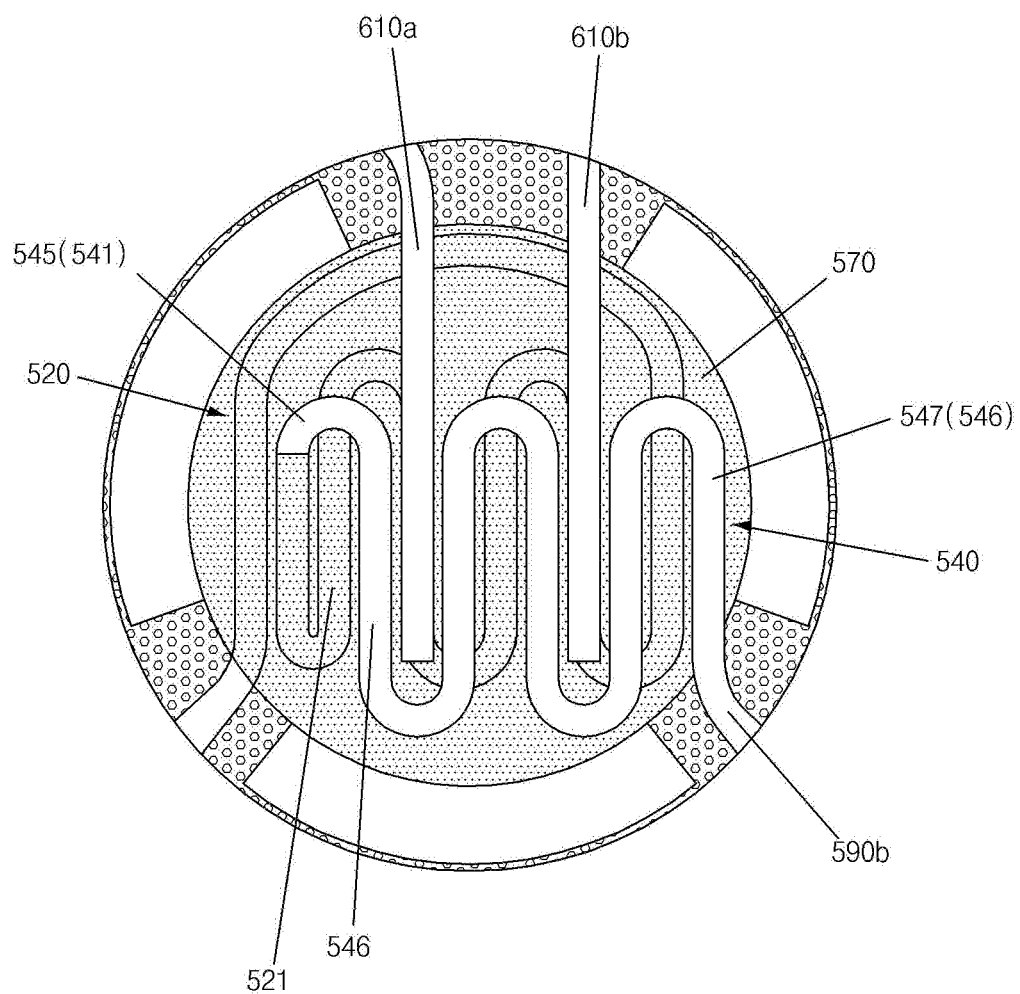
FIG. 12 is an enlarged plane view of a first support portion and an air gap portion (in which a sensing material and a protection layer are omitted).
Figure 13:
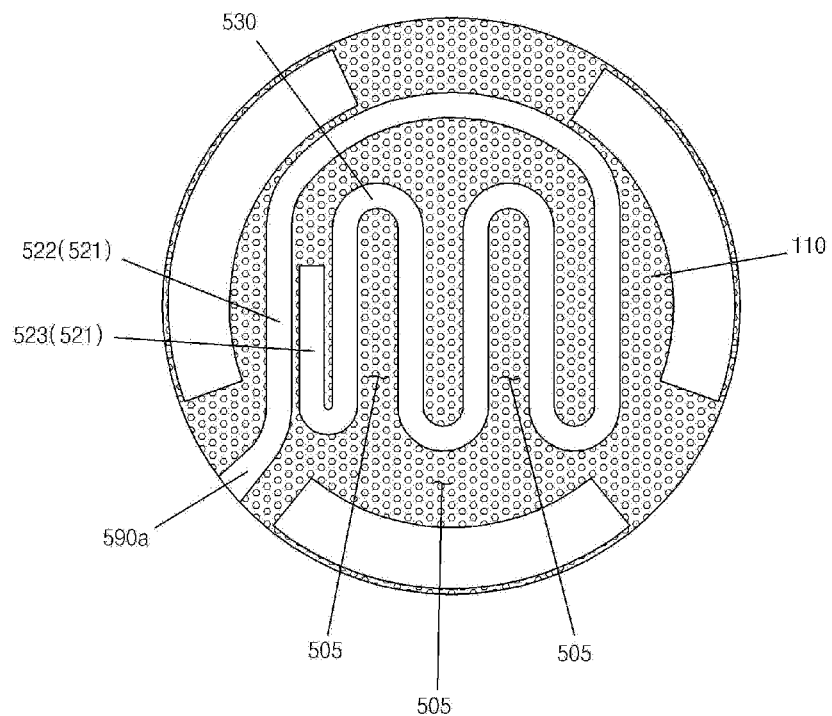
FIG. 13 is a plane view of the first support portion and the air gap portion illustrated in FIG. 12, from which a passivation layer, a second heat generation wiring line and a sensor wiring line are removed.

As illustrated in FIGS. 12 and 13, the first heat generation wiring line 520 and the second heat generation wiring line 540 are formed in mutually different patterns. The second heat generation wiring line 540 is formed in the first support portion 110 at the upper side of the space 505 where the first heat generation wiring line 520 is not disposed.

As illustrated in FIG. 13, the first heat generation wiring line 520 includes a plurality of straight line portions 521 formed in a straight line shape and spaced apart from each other, and a plurality of curvilinear portions 530 formed of a curved line having an inflection point and configured to interconnect end portions of the spaced-apart straight line portions 521. The first heat generation wiring line 520 is continuously formed by alternately and repeatedly interconnecting the straight line portions 521 and the curvilinear portions 530. The curvilinear portions 530 are connection portions configured to interconnect end portions of the straight line portions 521.

A first heater electrode pad 590a is connected to one end portion of an eleventh straight line portion 522 which is one of the straight line portions 521 of the first heat generation wiring line 520.

Figure 14:
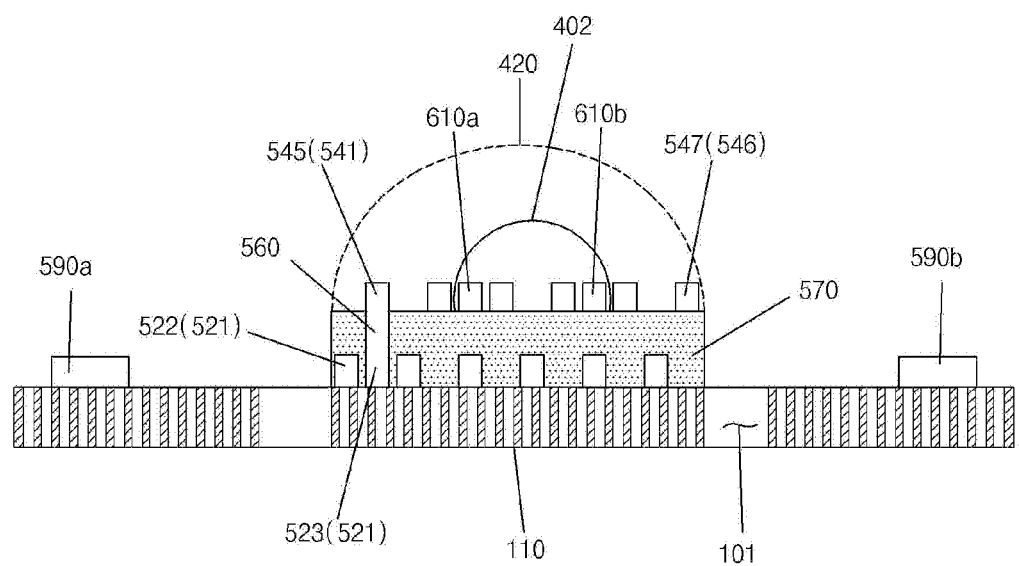
FIG. 14 is a sectional view taken along line A-A in FIG. 11.
Figure 15:
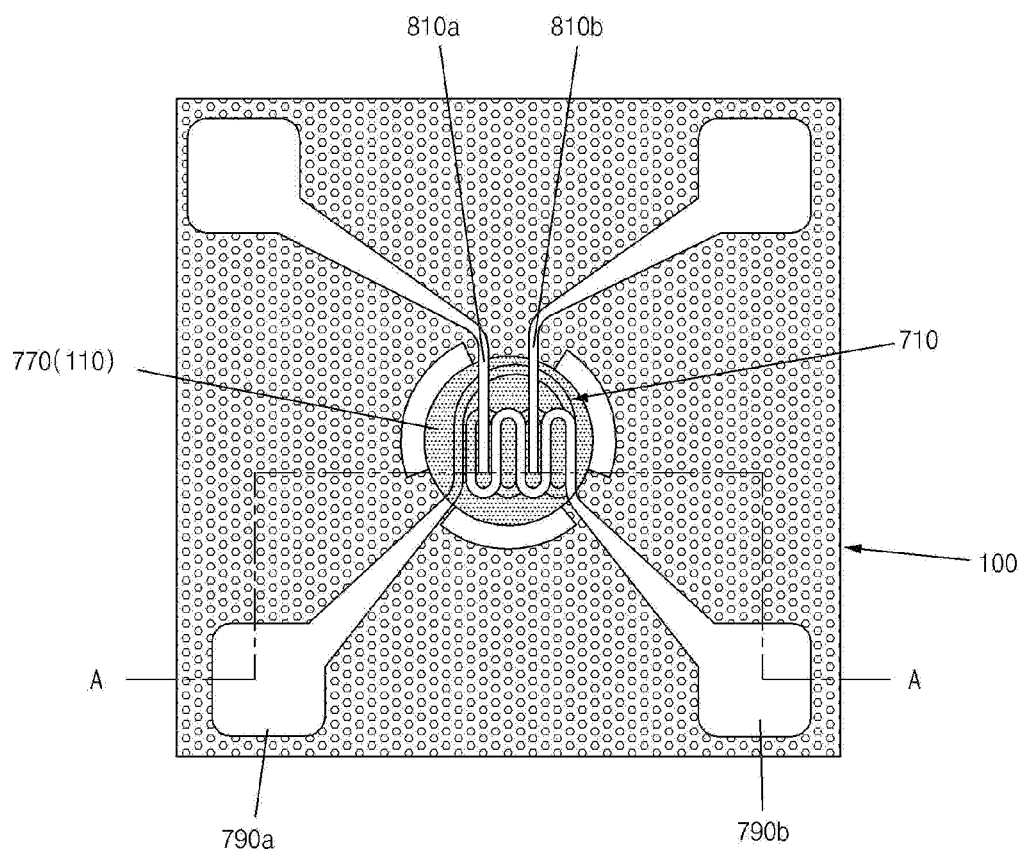
FIG. 15 is a plane view of a micro sensor provided with a micro heater according to a third preferred embodiment of the present invention (in which a sensing material and a protection layer are omitted).

As illustrated in FIG. 14, a connection wiring line 560 is vertically connected to one end portion of a twelfth straight line portion 523 adjoining the eleventh straight line portion 522. The upper end portion of the connection wiring line 560 is connected to one end portion of an eleventh curvilinear portion 545 of the second heat generation wiring line 540.

The second heat generation wiring line 540 is formed on the passivation layer 570. The second heat generation wiring line 540 includes a plurality of straight line portions 546 and a plurality of curvilinear portions 541 formed of a curved line having a deflection point and configured to interconnect end portions of the spaced-apart straight line portions 546. The second heat generation wiring line 540 is continuously formed by alternately and repeatedly interconnecting the straight line portions 546 and the curvilinear portions 541.

The second heat generation wiring line 540 is at least partially disposed at an upper side of a space 505 (see FIG. 13) where the first heat generation wiring line 520 is not disposed. Thus, as illustrated in FIG. 12, when seen in a plane view, the straight line portions 521 of the first heat generation wiring line 520 and the straight line portions 546 of the second heat generation wiring line 540 may be alternately disposed so as to stagger in a left-right direction.

A first sensor wiring line 610a and a second sensor wiring line 610b are formed between the spaced-apart straight line portions 546 of the second heat generation wiring line 540. A second heater electrode pad 590b is connected to one end portion of a thirteenth straight line portion 547 of the straight line portions 546 of the second heat generation wiring line 540.

The heat generation wiring line 510 is continuously formed in the order of the first heater electrode pad 590a, the first heat generation wiring line 520, the connection wiring line 560, the second heat generation wiring line 540 and the second heater electrode pad 590b.

Furthermore, a sensing material 402 is formed on the passivation layer 570 so as to cover the sensor wiring lines 610a and 610b.

As described above, the first heat generation wiring line 520 and the second heat generation wiring line 540 are laminated one above the other in mutually different patterns. It is therefore possible to uniformly heat the entirety of the first support portion 110, thereby ensuring the temperature uniformity. This makes it possible to uniformly heat the sensing material 402 existing on the first support portion 110.

Hereinafter, a micro sensor according to a third preferred embodiment of the present invention will be described with reference to FIGS. 15 to 18. Descriptions on the same components as those of the first embodiment and the second embodiment will be omitted. Only a heat generation wiring line 710 differing from that of the first embodiment and the second embodiment will be described.

The heat generation wiring line 710 according to the third embodiment includes a first heat generation wiring line 720 formed on the substrate 100, a second heat generation wiring line 740 at least partially formed at an upper side of a space 705 where the first heat generation wiring line 720 is not disposed, and a connection wiring line 760 configured to interconnect the first heat generation wiring line 720 and the second heat generation wiring line 740. A passivation layer 770 is formed between the first heat generation wiring line 720 and the second heat generation wiring line 740. Each of the first heat generation wiring line 720 and the second heat generation wiring line 740 includes a plurality of straight line portions 721 or 741 formed in a straight line shape and spaced apart from each other, and a plurality of curvilinear portions 730 or 750 configured to interconnect the straight line portions 721 or 741. The straight line portions 741 of the second heat generation wiring line 740 are laminated above the straight line portions 721 of the first heat generation wiring line 720. The curvilinear portions 730 or 750 are connection portions configured to interconnect end portions of the straight line portions 721 or 741.

Figure 16:
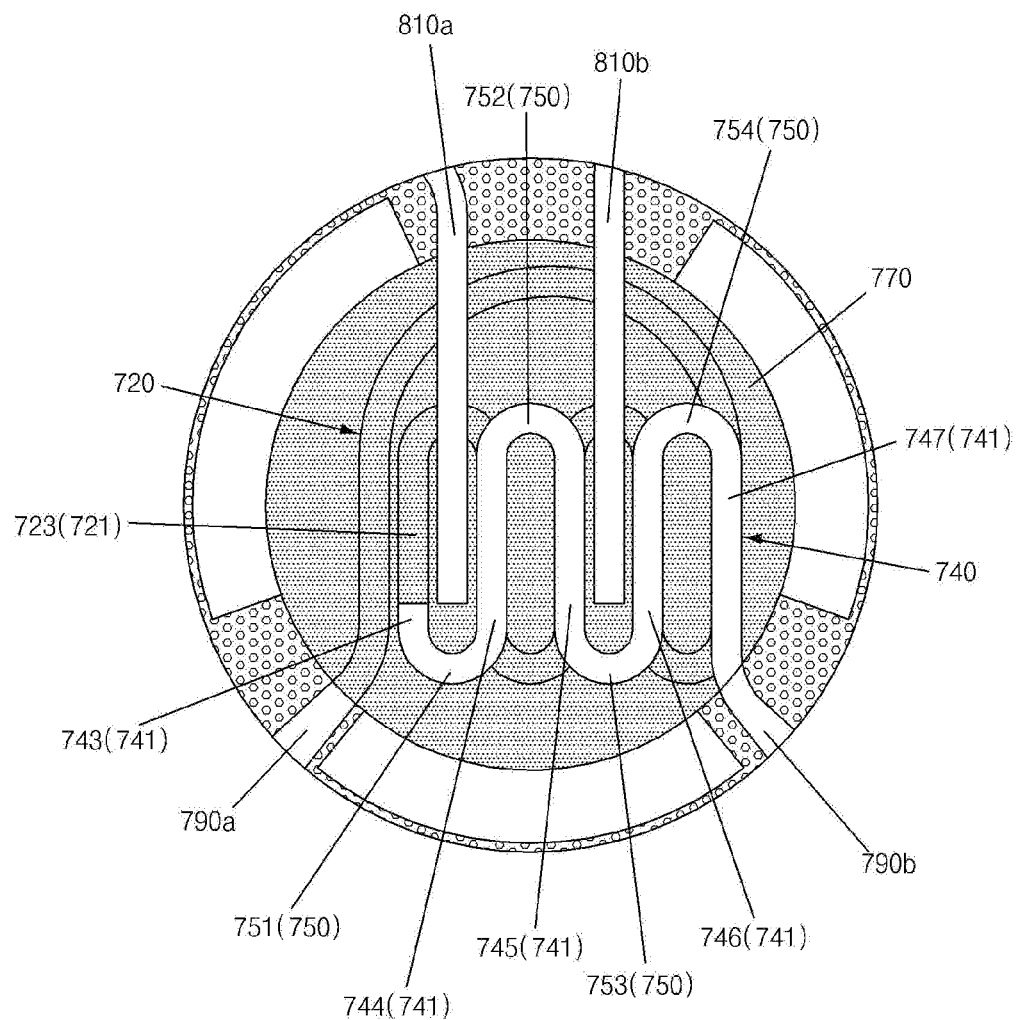
FIG. 16 is an enlarged plane view of a first support portion and an air gap portion (in which a sensing material and a protection layer are omitted).
Figure 17:
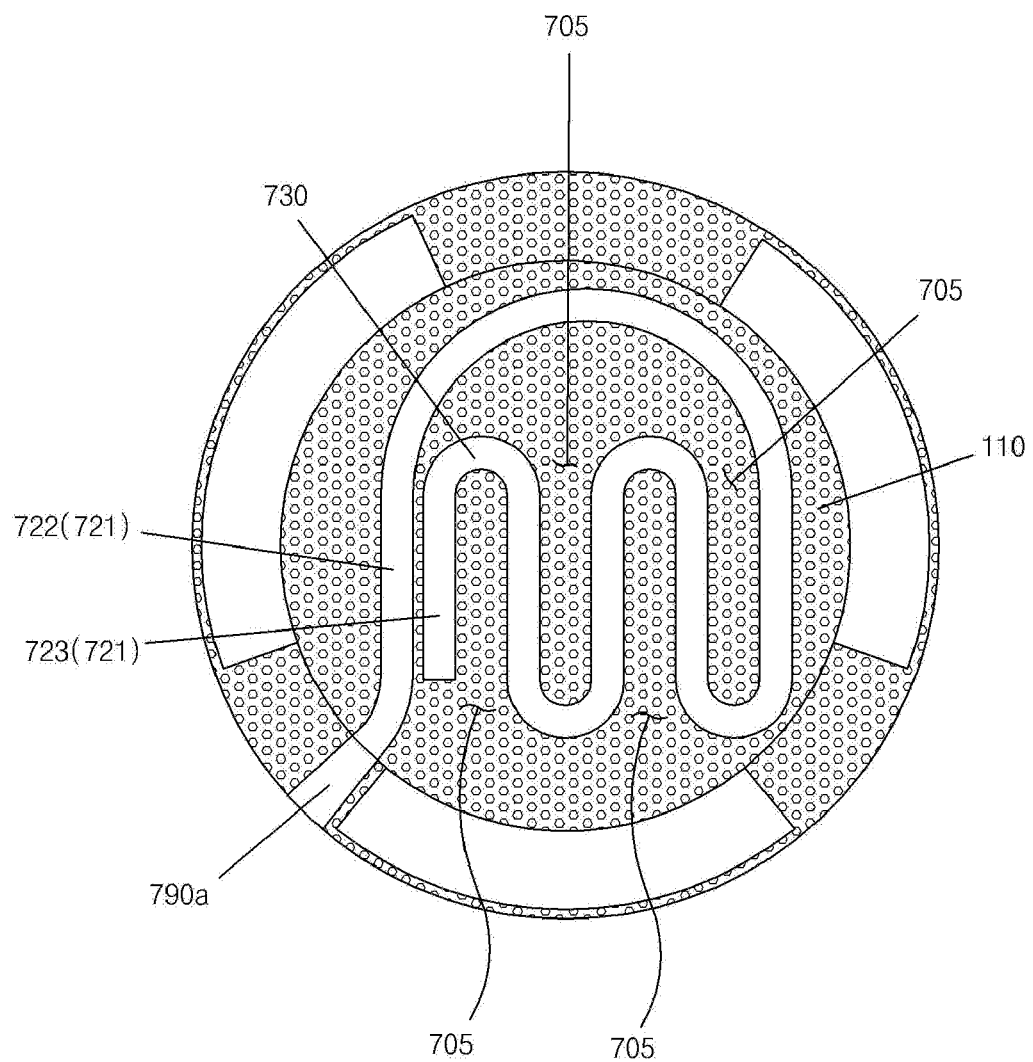
FIG. 17 is a plane view of the first support portion and the air gap portion illustrated in FIG. 16, from which a passivation layer, a second heat generation wiring line and a sensor wiring line are removed.

As illustrated in FIGS. 16 and 17, the first heat generation wiring line 720 and the second heat generation wiring line 740 are formed in mutually different patterns. The curvilinear portions 750 of the second heat generation wiring line 740 are formed in the first support portion 110 at the upper side of the space 705 where the first heat generation wiring line 720 is not disposed.

As illustrated in FIG. 17, the first heat generation wiring line 720 is formed in a pattern similar to the pattern of the first heat generation wiring line 520 of the second embodiment. The first heat generation wiring line 720 includes a plurality of straight line portions 721 formed in a straight line shape and spaced apart from each other, and a plurality of curvilinear portions 730 formed of a curved line having an inflection point and configured to interconnect end portions of the spaced-apart straight line portions 721. The first heat generation wiring line 720 is continuously formed by alternately and repeatedly interconnecting the straight line portions 721 and the curvilinear portions 730. The curvilinear portions 730 are connection portions configured to interconnect end portions of the straight line portions 721.

A first heater electrode pad 790a is connected to one end portion of a fourteenth straight line portion 722 which is one of the straight line portions 721.

Figure 18:
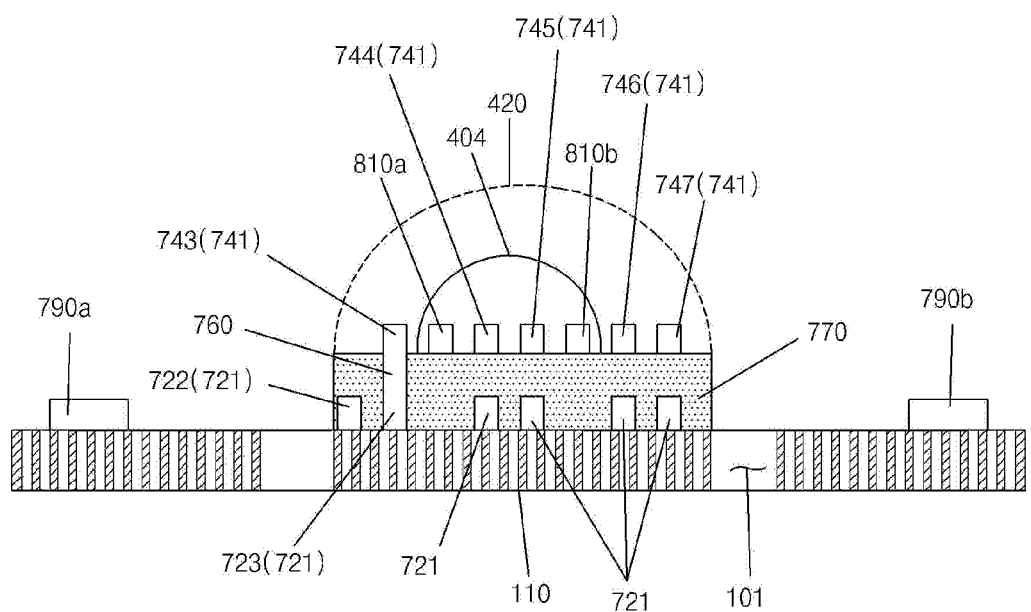
FIG. 18 is a sectional view taken along line A-A in FIG. 15.

As illustrated in FIG. 18, the connection wiring line 760 is vertically connected to one end portion of a fifteenth straight line portion 723 adjoining the fourteenth straight line portion 722. The upper end portion of the connection wiring line 760 is connected to one end portion of a sixteenth straight line portion 743 of the second heat generation wiring line 740.

The second heat generation wiring line 740 includes a plurality of straight line portions 741 formed on the passivation layer 770 and spaced apart from each other, and a plurality of curvilinear portions 750 formed of a curved line having an inflection point and configured to interconnect end portions of the spaced-apart straight line portions 741. The second heat generation wiring line 740 is continuously formed by alternately and repeatedly interconnecting the straight line portions 741 and the curvilinear portions 750.

When seen in a plane view, the straight line portions 741 are spaced apart at predetermined intervals and are disposed parallel to one another in the order of the sixteenth to twentieth straight line portions 743 to 747. The sixteenth straight line portion 743 is shorter in length than the seventeenth to twentieth straight line portions 744 to 747.

The twelfth curvilinear portion 751 is configured to interconnect the other end portion of the sixteenth straight line portion 743 and one end portion of the seventeenth straight line portion 744. The thirteenth curvilinear portion 752 is configured to interconnect the other end portion of the seventeenth straight line portion 744 and one end portion of the eighteenth straight line portion 745. The fourteenth curvilinear portion 753 is configured to interconnect the other end portion of the eighteenth straight line portion 745 and one end portion of the nineteenth straight line portion 746. The fifteenth curvilinear portion 754 is configured to interconnect the other end portion of the nineteenth straight line portion 746 and one end portion of the twentieth straight line portion 747.

Thus, the twelfth to fifteenth twelfth curvilinear portions 751 to 754 are formed in the first support portion 110 at the upper side of the space 705 where the first heat generation wiring line 720 is not disposed.

The twelfth curvilinear portions 750 of the second heat generation wiring line 740 is disposed at the upper side of the space 705 (see FIG. 17) where the first heat generation wiring line 720 is not disposed. Among the straight line portions 741 of the second heat generation wiring line 740, the straight line portions 744,745,746 and 747 other than the sixteenth straight line portion 743 are all laminated at the upper side of the straight line portions 721 of the first heat generation wiring line 720. In other words, the seventeenth to twentieth straight line portions 744 to 747 of the second heat generation wiring line 740 are laminated at the upper side of the straight line portions 721 of the first heat generation wiring line 720.

Furthermore, a first sensor wiring line 810a and a second sensor wiring line 810b are formed on the passivation layer 770. When seen in a plane view, the first sensor wiring line 810a is formed between the fifteenth straight line portion 723 and the seventeenth straight line portion 744 spaced apart from each other. The second sensor wiring line 810b is formed between the eighteenth straight line portion 745 and the nineteenth straight line portion 746.

A second heater electrode pad 790b is connected to the other end portion of the twentieth straight line portion 747 among the straight line portions 741 of the second heat generation wiring line 740.

The first heater electrode pad 790a, the first heat generation wiring line 720, the connection wiring line 760, the second heat generation wiring line 740 and the second heater electrode pad 790b are sequentially connected and continuously formed.

A sensing material 404 is formed on the passivation layer 770 so as to cover the sensor wiring lines 810a and 810b.

Hereinafter, the operation of the micro sensor configured as above will be described.

In order to measure a gas concentration, predetermined electric power is applied to two heater electrode pads 290 of the heater electrode 200 to heat the sensing material 400, 402 or 404 of the central portion of the micro sensor to a predetermined temperature.

In this state, a change in the characteristics of the sensing material 400, 402 or 404 generated when a gas existing around the micro sensor is adsorbed to or desorbed from the sensing material 400, 402 or 404 in a corresponding relationship thereof is measured by measuring an electric potential difference between the sensor electrode pads 320 electrically connected to the sensing material 400, 402 or 404 through the use of an external circuit and quantifying the electric conductivity of the sensing material 400, 402 or 404.

For the sake of accurate measurement, other gas species and moisture already adsorbed to the sensing material 400, 402 or 404 are heated to a high temperature by the heater electrode 200 and are forcibly removed, thereby restoring the sensing material 400, 402 or 404 to an initial state. Thereafter, the concentration of a gas of interest is measured.

While preferred embodiments of the present invention have been described above, a person skilled in the relevant technical field will be able to diversely change or modify the present invention without departing from the spirit and scope of the present invention defined in the claims.

What is claimed is:

1. A micro heater, comprising:
   a substrate having an upper surface and a lower surface and including a first support portion;
   a heater electrode formed on the substrate and provided with a heat generation wiring line supported by the first support portion; and
   a plurality of air gaps formed in the substrate around the heat generation wiring line, wherein the air gaps are formed discontinuously around the periphery of the first support portion among the regions excluding the portion supporting the heater electrode and includes a space formed penetrating from the upper surface to the lower surface of the substrate,
   wherein the heat generation wiring line includes at least a first heat generation wiring line and a second heat generation wiring line laminated along the up-down direction,
   wherein a passivation layer is formed between the first heat generation wiring line and the second heat generation wiring line,
   wherein the substrate is formed of an aluminum oxide porous layer,
   characterized in that the aluminum oxide porous layer is formed to form pores penetrating from the upper surface to the lower surface of the substrate.

2. The micro heater of claim 1, wherein the first heat generation wiring line is formed on the substrate, the second heat generation wiring line is laminated above the first heat generation wiring line, and the heat generation wiring line further includes a connection wiring line configured to interconnect the first heat generation wiring line and the second heat generation wiring line.

3. The micro heater of claim 1, wherein the first heat generation wiring line is formed on the substrate, the second heat generation wiring line is at least partially formed at an upper side of a space where the first heat generation wiring line is not disposed, and the heat generation wiring line further includes a connection wiring line configured to interconnect the first heat generation wiring line and the second heat generation wiring line.

4. A micro sensor, comprising:
a substrate having an upper surface and a lower surface and including a first support portion;
a sensor electrode formed on the substrate; and
a heater electrode formed on the substrate and provided with a heat generation wiring line supported by the first support portion; and
a plurality of air gaps formed in the substrate around the heat generation wiring line,
wherein the air gaps are formed discontinuously around the periphery of the first support portion among the regions excluding the portion supporting the heater electrode and includes a space formed penetrating from the upper surface to the lower surface of the substrate,
wherein the heat generation wiring line is includes at least a first heat generation wiring line and a second heat generation wiring line laminated along the up-down direction,
wherein a passivation layer is formed between the first heat generation wiring line and the second heat generation wiring line,
wherein the substrate is formed of an aluminum oxide porous layer, characterized in that the aluminum oxide porous layer forms pores penetrating from the upper surface to the lower surface of the substrate.

5. The micro sensor of claim 4, wherein the first heat generation wiring line is formed on the substrate, the second heat generation wiring line is laminated above the first heat generation wiring line, and the heat generation wiring line further includes a connection wiring line configured to interconnect the first heat generation wiring line and the second heat generation wiring line.

6. The micro sensor of claim 4, wherein the first heat generation wiring line is formed on the substrate, a second heat generation wiring line is at least partially formed at an upper side of a space where the first heat generation wiring line is not disposed, and the heat generation wiring line further includes a connection wiring line configured to interconnect the first heat generation wiring line and the second heat generation wiring line.

* * * * *